United States Patent [19]

Ferres et al.

[11] 3,957,759

[45] May 18, 1976

[54] PENICILLINS

[75] Inventors: Harry Ferres, Horsham; Adrian Victor Kemmenoe, Westcott; Desmond John Best, Sutton, all of England

[73] Assignee: Beecham Group Limited, Great Britain

[22] Filed: May 19, 1975

[21] Appl. No.: 578,722

Related U.S. Application Data

[62] Division of Ser. No. 466,814, May 3, 1974.

[30] Foreign Application Priority Data

May 4, 1973 United Kingdom............... 21203/73

[52] U.S. Cl.............................. 260/239.1; 424/271
[51] Int. Cl.²....................................... C07D 499/68
[58] Field of Search.................................. 260/239.1

[56] References Cited

UNITED STATES PATENTS

| 3,340,252 | 9/1967 | Alburn et al..................... 260/239.1 |
| 3,483,188 | 12/1969 | McGregor........................ 260/239.1 |

*Primary Examiner*—Gerald A. Schwartz

[57] ABSTRACT

New penicillins and their salts and esters particularly active against Gram-negative organisms such as Pseudomonas spp., and their preparation and administration. The penicillins are active against clinically important organisms against which well-known broad spectrum penicillins are inactive and may generally be designated as aminoacyldipeptide penicillins of unusual structure and properties.

8 Claims, No Drawings

PENICILLINS

CROSS-REFERENCE

This is a division of Serial No. 466,814 filed May 3, 1974.

This invention relates to penicillins which have, in general, a broad spectrum of antibacterial activity, being active against many species of Gram-positive and Gram-negative bacteria. They are thus useful as therapeutic (and, to a lesser extent, prophylactic) agents in animals, including man and poultry. The invention further relates to methods for the preparation of these penicillins and to their use in therapy.

Although there are now available a number of semi-synthetic penicillins having what is known as broad-spectrum activity, no single penicillin is yet available which has a clinically useful level of antibacterial activity against all the pathogenic organisms encountered in clinical practice. The search thus continues for broad-spectrum penicillins which have advantages, either in improved antibacterial effectiveness or wider spectrum of activity, over the available penicillins.

According to the present invention there is provided a penicillin of formula (I) or a pharmaceutically acceptable salt or ester thereof:

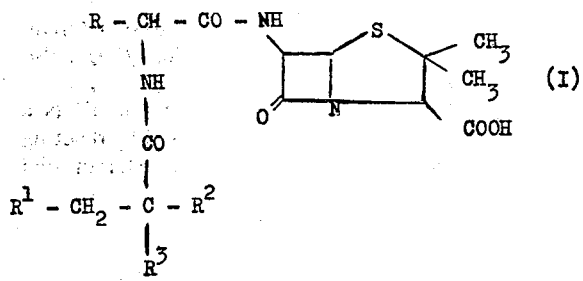

wherein
R is phenyl, phenyl substituted by one or more functional groups selected from hydroxy, halogen, nitro, alkoxy containing from 1 to 3 carbon atoms, and amino groups, 2- or 3-thienyl, cycloalkyl having from 3 to 7 carbon atoms, cycloalkenyl having from 5 to 7 carbon atoms or alkyl having from 1 to 4 carbon atoms;
$R^3$ is hydrogen or an alkyl group having from 1 to 3 carbon atoms; $R^1$ is hydrogen or an organic radical containing up to 20 carbon atoms;
$R^2$ is a group of formula (II) or (III):

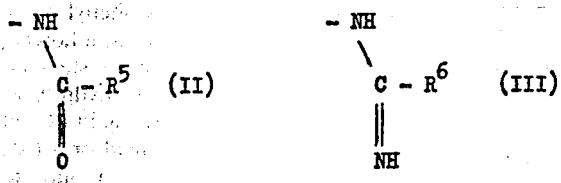

wherein $R^5$ is amino, mono-or di-alkylamino wherein the alkyl groups contain from 1 to 4 carbon atoms, cyclohexylamino, hydrogen, alkyl having from 1 to 4 carbon atoms, or phenyl and $R^6$ is amino or mono- or di-alkylamino wherein the alkyl groups contain from 1 to 4 carbon atoms, or cyclohexylamino.

The group R may be, for example, phenyl, 4-hydroxyphenyl, 3-chloro-4-hydroxyphenyl, 4-nitrophenyl, 4-chlorophenyl, 4-fluorophenyl, 4-methoxy-phenyl, 4-aminophenyl, 2-thienyl, 3-thienyl, cyclopropyl, cyclohexyl, cyclohexa-1,4-dienyl, iso-propyl or methyl.

The group $R^1$ may, for example, be hydrogen, phenyl, 4-hydroxyphenyl, 4-nitrophenyl, 4-chlorophenyl, 4-fluorophenyl, 4-methoxyphenyl, 4-aminophenyl, methyl, ethyl, n-propyl, isopropyl, n-butyl, isobutyl, tert-butyl, methoxy, ethoxy, n-propoxy, isopropoxy, methylene, ethylene, ethylthio, n-propoxy-methyl, carbamyl, carbamylmethyl, acetoxy, phenoxy, benzyloxy, 2-thienyl, 3-thienyl, indol-3-yl, 1H-imidazol-5-yl, cyclohexa-1,4-dienyl, cyclopropyl or cyclohexyl.

The group $R^5$ may, for example, be amino, methylamino, n-butylamino, tert-butylamino, cyclohexylamino, hydrogen, methyl, ethyl, n- or isopropyl, n-, sec, or tert-butyl, or phenyl.

The group $R^6$ may for example, be amino, methylamino, dimethylamino, ethylamino, isopropylamino, n-propylamino, iso-propylamino, tert-butylamino, n-butylamino or cyclohexylamino.

Preferably R is phenyl, 4-hydroxyphenyl, or 3-thienyl.

Preferably $R^1$ is phenyl, 4-hydroxyphenyl, 4-chlorophenyl, 4-fluorophenyl, 4-nitrophenyl, 3-indolyl, or methylthiomethyl.

Preferably $R^3$ is hydrogen.

Preferably $R^5$ is amino or hydrogen.

Preferably $R^6$ is amino.

Preferably the carbon atom to which the group R in formula (I) is attached is in the D configuration.

Preferably the carbon atom to which the group $R^2$ in formula (I) is attached is in the D configuration.

Examples of suitable salts of compounds (I) include the sodium, potassium, calcium, magnesium or aluminium salts, and ammonium or substituted ammonium salts, for example those with trialkylamines such as triethylamine, procaine, dibenzylamine, triethanolamine, 1-ephenamine, ethylpiperidine, and other amines which have been used to form salts with benzylpenicillins. In the case of compounds (I) which contain a basic nitrogen site in the side chain, acid addition salts may also be formed. Such salts include, for example, inorganic slats such as the sulphate, nitrate, phosphate, borate, thiocyanate, and hydrohalides, e.g. hydrochloride, hydrobromide and hydroiodide, and organic salts such as the acetate, oxalate, tartrate, malate, citrate, succinate, benzoate, ascorbate and methanesulphonate.

Examples of suitable pharmaceutically acceptable esters include those which break down readily in the human body to leave the parent acid, e.g. acyloxyalkyl esters such as acetoxymethyl, pivaloyloxymethyl, α-acetoxyethyl, α-acetoxybenzyl and α-pivaloyloxymethyl esters, and alkoxycarbonylalkyl esters such as methoxy carbonyloxymethyl esters. Other suitable esters of this readily hydrolysable type include lactone, thiolactone, and dithiolactone esters (i.e. compounds of formula (I) wherein the 3-carboxy group is esterified to produce a grouping of formula:

$$- CO - O - CH - Z^1$$
$$\qquad\qquad |\qquad |$$
$$\qquad\qquad X^1 - C = Y^1$$

wherein $X^1$ and $Y^1$ are oxygen or sulphur and $Z^1$ is a divalent hydrocarbon group), especially the phthalidyl and substituted phthalidyl esters e.g. 5,6-dimethoxyphthalidyl ester.

The compounds of this invention may be prepared by reacting 6-aminopenicillanic acid or a salt, ester or silyl derivative thereof with an N-acylating derivative of an acid of formula (IV)

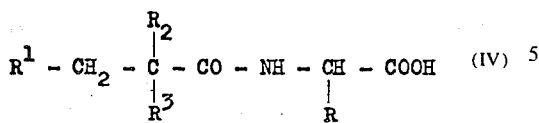

in which any reactive substituents may be blocked, wherein R, R$^1$, R$^2$ and R$^3$, are as defined in formula (I) and then, if necessary, carrying out one or more of the following steps (i) removing any silyl groups by hydrolysis or alcoholysis, (ii) converting an ester compound to a free acid or salt (iii) converting a salt to a free acid or a free acid to a salt (iv) removing any blocking groups to release the desired functional substituent (v) converting a free acid compound to an ester compound.

By the term "silyl derivative" used in connection with 6-amino-penicillanic acid (6-APA) we mean the product of the reaction between 6-APA and a silylating agent such as a halotrialkylsilane, halodialkylsilane, a halotrialkoxysilane, a dihalodialkoxysilane or a corresponding aryl or aralkyl silane and compounds such as hexamethyldisilazane. In general, halotrialkylsilanes are preferred, especially trimethylchlorosilane.

A reactive N-acylating derivative of the acid (IV) is employed in the above process. The choice of reactive derivative will of course be influenced by the chemical nature of the substituents in the acid. Thus, when the acid contains only acid stable groups, an acid halide is a suitable N-acylating derivative, preferably the acid chloride.

Such reagents would, however, be avoided when an acid labile group was present in the acid (IV). In such cases a suiable N-acylating derivative is a mixed anhydride. For this purpose particularly convenient mixed anhydrides are the alkoxyformic anhydrides.

However, with both the acid chloride and mixed anhydride N-acylating agents we have found that some racemisation may take place. To minimise such unwanted racemisation, we prefer to use an activated ester as the N-acylating agent. Such activated esters, for example the ester formed with 1-hydroxybenzotriazole or, preferably, N-hydroxysuccinimide, may be prepared in situ by the reaction of the acid with the appropriate hydroxy compound in the presence of a carbodiimide, preferably dicyclohexylcarbodiimide.

Other reactive N-acylating derivatives of the acid (II) include the reactive intermediate formed by reaction in situ with a carbodiimide or carbonyldiimidazole, but the literature on the preparation of semi-synthetic penicillins contains examples of other reactive N-acylating derivatives of acids suitable for coupling to 6-APA.

It will be understood, of course, that where a free acid of type (I) or a salt thereof is desired, it may be convenient to carry out the acylation reaction using an ester of 6-APA, and then to remove the ester group. Vice versa, if an ester is required, it may be convenient to carry out the acylation reaction using 6-APA or a salt thereof and thereafter to esterify the free acid.

In the above process, if it is necessary to block any reactive substituents in the acid (IV), conventional chemical blocking groups are known. Thus, if desired, any free amino groups may be blocked by conversion to benzyloxycarbonylamino groups, or the amino group may be blocked as the nitro group which is later converted to the amino group.

The compounds of this invention may also be prepared by a process which comprises reacting a compound of formula (V) or a salt, ester or silyl derivative thereof.

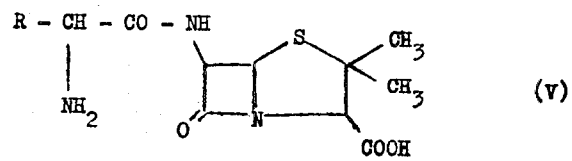

wherein R is as defined in formula (I) and in which any reactive substituents may be blocked, with an N-acylating derivative of an acid of formula (VI)

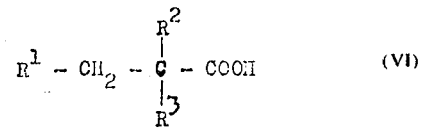

wherein R$^1$, R$^2$ and R$^3$ are as defined in formula (I), and if necessary, carrying out one or more of the following steps (i) removing any silyl groups by hydrolysis or alcoholysis, (ii) converting an ester compound to a free acid or salt thereof (iii) converting a salt to a free acid or a free acid to a salt (iv) removing any blocking groups to release the desired functional substituents (v) converting a free acid compound to an ester compound.

The remarks made earlier with respect to silyl derivatives, N-acylating derivatives, and blocking groups, also apply to this process.

The compounds of this invention wherein R$^1$ is a group of formula (II) may also be prepared by reacting a compound of formula (VII) or a salt, ester or silyl derivative thereof:

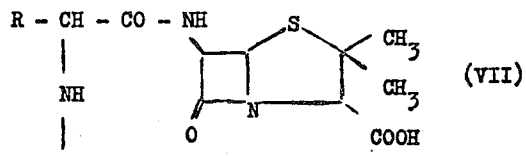
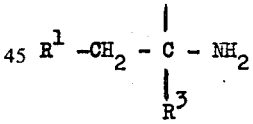

wherein R, R$^1$, R$^3$ and R$^4$ are as defined in formula (I) and wherein any reactive substituents may be blocked, with cyanate ion, a C$_{1-4}$ alkyl isocyanate, cyclohexyl isocyanate, a formylating agent or an N-acylating derivative of an acid R$^6$COOH wherein R$^6$ is phenyl or an alkyl group having from 1 to 4 carbon atoms, followed, if necessary, by one or more of the following steps (i) removing any silyl groups by alcoholysis or hydrolysis, (ii) converting an ester compound to free acid or salt thereof, (iii) converting a salt to a free acid or a free acid to a salt (iv) removing any blocking groups to release the desired functional substituent, (v) converting a free acid compound to an ester compound.

It will be noted that the above process essentially consists in generating the desired group R$^2$ from the free amino group in compound (VII). The reaction of amino compounds with cyanate ion and isocyanates to produce ureas and substituted ureas is well known. Likewise the formylation of amino compounds (e.g. using formic acid and acetic anhydride) is well known. Similarly, the acylation of amino compounds is extremely well known, and suitable N-acylating derivatives of acids have been discussed hereinbefore.

The compounds of this invention are broad spectrum penicillins, i.e. penicillins which not only have activity against Gram-positive bacteria, but also against a number of clinically important Gram-negative organisms. The preferred compounds of this invention are active against such important organisms as Pseudomonas spp. against which the most well known broad-spectrum penicillin (6[(D)α-aminophenylacetamido]penicillanic acid . . . ampicillin) is normally inactive. Moreover the preferred compounds of this invention are about as active as 6[(D)α-carboxy-3-thienylacetamido] penicillanic acid against Pseudomonas spp., this latter compound being the most active of the known penicillins against those organisms. Several of the preferred compounds of this invention have minimum inhibitory concentrations of from 5–12.5 μg/ml against some β-lactamase producing strains of staphylococci, against which the majority of known broad spectrum penicillins are only marginally effective. The preferred compounds of this invention are not greatly serum-bound, and are not markedly inactivated by serum.

The penicillins of this invention show the characteristic lack of toxicity of penicillins generally. They may be administered by parenteral injection. The daily dose will depend on the identity of the penicillin and severity of infectioon. With the preferred compounds of this invention, a suitable average daily dose for an adult would be in the range of 100mg to 5000mg. An average single dose for an adult would be from 20 mg to 500 mg.

The following Examples illustrate the preparation of some of the compounds of this invention:

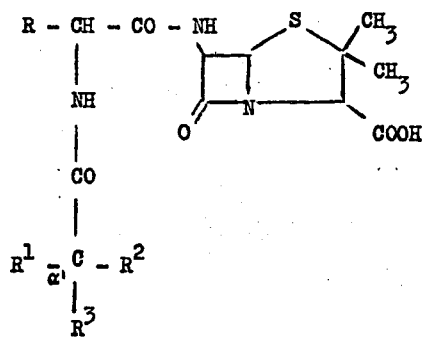

In the following Examples amoxycillin is the approved name for 6[D-α-amino-p-hydroxyphenylacetamido]penicillanic acid and ampicillin is the approved name for 6[D-α-aminophenylacetamido] penicillanic acid. Epicillin is the approved name for [D-α-amino -cyclohexa-1,4-dienylacetamido]penicillanic acid. All temperatures are in °C. All biochromatograms were run in butanol/ethanol/water. All compounds were made by one of the following generally applicable methods.

The majority of the starting materials used in the following Examples are known. However, the following literature references described generally applicable methods which may be used to prepare the starting materials:

UREIDO-ACIDS

| | |
|---|---|
| DAKIN | Amer. Chem. J. 44 54 |
| ANDREASCH | Monats. 23. 805 |
| NEVILLE, McGEE | Can. J. Chem. 41, 2123–9 (1963) |
| WIELAND | Bio. Z. 38, 389, Ann. 3. |
| DAVIS, BLANCHARD | J. Amer. Chem. Soc. 51, 1797 |
| LEUTHARDT, BRUNNER | Helv. Chim. Acta. 30, 964–5 (1947) |

SUBSTITUTED UREIDO-ACIDS

| | |
|---|---|
| BALL, SKINNER, SHIVE | Texas Rept. Biol. Med. 21(2) 188–75 (1963) |
| BRITISH PATENTS 1301961/2.2 | |

GUANIDINO-ACIDS

| | |
|---|---|
| KAPFHAMMER, MILLER | Z. Physiol, Chem. 225, 1–12, (1934) |
| RADKA PANT | Ibid 335, 272–4 (1964) |
| FRAMM, KAPELLER | Ann. (1925) 442, 144 |
| HABEL | Can. J. Biochem. Physiol. 38, 493 (1960) |
| RAMSAY | Ber. 41, 4390 |

FORMAMIDO-ACIDS

| | |
|---|---|
| SHEEHAN, YOUNG | J. Amer. Chem. Soc. (1958), 80, 1154 |

Method A

A solution of the guanidino-acid, hydrochloride (5 m. mole) in dry dimethylformamide (5 ml) was added over 10 mins. to a stirred solution of phthalid-3-yl D-α-aminophenyl-acetamidopenicillanate (5 m. mole) and N,N¹-dicyclohexylcarbodi-imide (5.8 m. mole) at 0° C in dry methylene dichloride.

After stirring at 0° C for 30 mins. and 1½ hours at ambient temperatures, the mixture was cooled to −10° C and the dicyclohexylurea removed by filtration.

The solution was washed with dilute hydrochloric acid (pH 1.5), water, and brine and the dried solution concentrated to low volume in vacuo to induce crystallisation. The filtered solid was dried under vacuum over phosphorus pentoxide.

Method B

Ureido- (or substituted-ureido-) acid (0.01 mole) in dry acetone (60 ml) at −10° C was treated with triethylamine (ca. 0.015 mole) and iso-butylchloroformate (0.01 mole) and stirred at −10° C for not more than 30 mins. D-α-aminophenylacetamidopenicillanic acid, trihydrate (0.01 mole) in water (60 ml) was treated with triethylamine to give a clear solution (pH 8.4). Acetone (60 ml) was added and the solution cooled to 0° C.

The mixed anhydride solution cooled to −40° C was filtered through Celite into the stirred penicillin solution and the mixture allowed to warm slowly to room temperature over 20 mins.

The acetone was evaporated in vacuo and the aqueous residue washed well with ether and then acidified to pH2 under a layer of ethyl acetate with 5N hydrochloric acid.

The product was obtained either as the free acid by filtration of the aqueous/ethyl acetate mixture or by precipitation from the ethyl acetate solution with potassium or sodium 2-ethylhexoate to give the corresponding alkali-metal salt.

Method Bi) As B, but using N-methylmorpholine instead of triethylamine in the preparation of the mixed anhydride.

Method Bii) As B, but using D-α-amino-(p-hydroxyphenyl)acetamidopenicillanic acid, trihydrate instead of D-α-aminophenylacetamidopenicillanic acid, trihydrate.

Method Biii) As Bii) but using N-methylmorpholine instead of triethylamine in the preparation of the mixed anhydride.

Method Biv) As Bi), but using D-α-amino-(3-thienyl)-acetamidopenicillanic acid instead of D-α-aminophenylacetamidopenicillanic acid, trihydrate.

Method Bv) As Bi), but using D-α-amino-(1,4-cyclohexadienyl)acetamidopenicillanic acid instead of D-α-aminophenylacetamidopenicillanic acid, trihydrate.

Method Bvi) As Bi), but using ethylchloroformate instead of iso-butyl chloroformate and D-α-aminocyclopropylacetamidopenicillanic acid, trihydrate.

Method Bvii) as Bi), but using D-α-aminovaleramidopenicillanic acid instead of D-α-aminophenylacetamidopenicillanic acid, trihydrate.

Method Bviii) As Bi), but using ethylchloroformate instead of isobutyl chloroformate, and D-α-amino-(2-thienyl)-acetamidopenicillanic acid instead of D-α-aminophenylacetamidopenicillanic acid, trihydrate.

Method Bix) As Bi), but using D-α-amino-β-phenylpropionamidopenicillanic acid instead of D-α-aminophenylacetamidopenicillanic acid. (No Method C)

Method D

Amino-penicillin (5 m. moles) in dry dimethylformamide (100ml) was treated with triethylamine (12 m. moles) and stirred to give a clear solution. Sulphur trioxide-triethylamine complex (6 m. moles) was added portionwise over 5 mins. at room temperature and stirred for 1 hour. A solution of potassium 2-ethyl hexoate (ca 15 m. moles) in dry acetone (150ml) was added and a white solid separated.

After further dilution with acetone (200ml) the solid was filtered, washed with acetone and then stirred in dry ether for 20 mins. to remove any residual dimethylformamide. The solid was filtered and dried in vacuo.

Method E

Anhydrous D-α-aminophenylacetamidopenicillanic acid (5 m. mole) in dry methylene dichloride (50ml) was treated with triethylamine (~10 m. mole) to give a clear solution. Trimethylsilyl chloride (10 m. mole) was added and the mixture refluxed under nitrogen for 1 hour, then cooled to 0° C.

α-Guanidino-acid (5 m. mole) was dissolved in dry dimethylformamide 55ml) and dry dimethylformamide (5ml.) and dry methylene dichloride (50 ml) added, cooled to 0° C and stirred for 5 mins. with dicyclohexylcarbodi-imide (5.5 m. mole). The bis-trimethylsilylated penicillin was added and stirred at 0° C for 1 hour. The mixture was then cooled to −20° C and the dicyclohexylurea removed by filtration. The filtrate was evaporated to dryness in vacuo and the residue dissolved in acetone (20ml)/water (20ml) and the pH adjusted to 2.5 with 5N hydrochloric acid. After stirring at pH 2.5 for 25 mins. The acetone was removed in vacuo and any solid filtered off. The residual aqueous solution was freeze dried and the resultant solid treated with water at pH 2. The product was filtered and dried.

Method F

Dicyclohexylcarbodi-imide (5.5 m. mole) was added to a stirred solution of N-substituted-amino acid (5 m. mole) in dry acetone (20 ml) at 0° C. The mixture was stirred for 15 mins. at 0°–5° C and then left in the refrigerator overnight.

D-α-Aminophenylacetamidopenicillanic acid, trihydrate (5 m. mole) was dissolved in acetone (10 ml)/water (10ml) with triethylamine (0.7 ml) and the hydroxysuccinimide ester filtered in, through Celite. After stirring for 45 mins. the acetone was removed in vacuo, leaving a gelatinuous mass. Acidification with 5N hydrochloric acid in aqueous ethyl acetate gave the product as the free acid (sometimes only after concentration of the ethyl acetate layer and treatment with ether) or as the salt by treatment of the washed and dried ethyl acetate layer with sodium or potassium 2-ethyl hexoate.

Method Fi) As F, but the hydroxysuccinimide ester formed in dry dimethylformamide (or dimethylformamide diluted with acetone).

Method Fii) As F, but the hydroxysuccinimide ester formed in dry 1,2-dimethoxyethane.

Method Fiii) As Fi), but the penicillin dissolved in acetone/chloroform, the product coming out of solution as the amine salt.

EXAMPLE 1

D-α-[D-β-(p-Hydroxyphenyl)-α-ureidopropionamido]phenylacetamido penicillanic acid (R = Ph; $R^1$ = -p—HO—PhCH$_2$; $R^3$ = H; $R^2$ = NHCONH$_2$; M = H; $\alpha^1$ = D).

Prepared by method Bi), from D-β-(p-Hydroxyphenyl)-α-ureidopropionic acid.

Yield: 68%. νmax (KBr): 3350, 1770, 1650, 1515, 1230 and 700cm$^{-1}$. δ[(CD$_3$)$_2$SO]: 1.44 (3H. s. gem methyl); 1.57 (3H s. gem methyl); ~2.8 (2H. m. -CH$_2$CH<); 4.29 (1H. s. C-3 proton); ~4.5 (1H. m. -CH$_2$CH<); 5.35 – 5.87 (5H. m. β-lactams, PhCH<; NHCONH$_2$*) 6.27 (1H. d. NHCONH$_2$*); 6.67

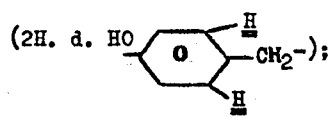

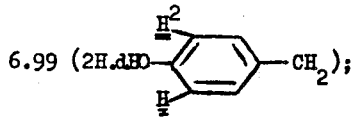

7.30 (5H. broad s. PhCH<); 8.47 (1H. m. -CONH*); 9.12 (1H. m. -CONH*).
*Removable in D₂O.

NH₂OH Assay: 101%. Biochromatography: 1 zone at R_f 0.32.

EXAMPLE 2

D-α-[D-β-(-p-Hydroxyphenyl)-α-ureidopropionamido]-(-p-hydroxyphenyl) acetamidopenicillanic acid.

(R = —p—HO—Ph; R¹ = —p—HO—PhCH₂; R³ = H; R² = NHCONH₂; M=H; α¹ = D).

Prepared by method Bi), from D-β-(-p-hydroxyphenyl)β-ureidopropionic acid and amoxycillin.

Yield: 74%. νmax (KBr): 3350 (broad), 1770, 1650, 1515, 1230 and 840 cm⁻¹. δ[(CD₃)₂SO]: 1.42 (3H. s. gem methyl); 1.57 (3H. s. gem methyl); ~2.8 (2H. m. —CH₂CH<); 4.3 (1H. s. C-3 proton); ~4.4 (1H. m. CH₂CH<); 5.3 - 5.85 (5H. m. β-lactams, Ph CH-; NHCONH₂*); 6.25 - 7.30 (8H. m. aromatics protons); 8.47 (1H. m. CONH*-); 9.12 (1H. m. -CONH*-).
* Removable in D₂O.

NH₂OH assay: 94%. Biochromatography: 1 zone at R_f = 0.18.

EXAMPLE 3

D-α-[D-β-(p-Hydroxyphenyl)-α-ureidopropionamido](3-thienyl)actamido penicillanic acid.

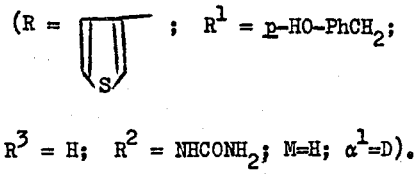

Prepared by method Bii), from D-β-(p-hydroxyphenyl)-α-ureidopropionic acid and α-amino-(3-thienyl) acetamido pencillanic acid.

Yield: 72% νmax (KBr): 3350 (broad); 1770, 1650, 1515, 1230, 845 and 780cm⁻¹. δ[(CD₃)₂SO]: 1.45 (3H. s. gem methyl); 1.58 (3H. s. gem methyl); ~2.8 (2H. m. -CH₂CH<); 4.3 (1H. s. C-3 proton), ~4.4 (1H. m. -CH₂CH<); 5.35 - 5.90 (5H. m. β-lactams, Ph -CH-; NHCONH₂*); 6.25 (1H. m. NH CONH₂); 6.5 - 7.6 (7H. m. aromatics); 8.5 (1H. d. CONH*); 9.1 (1H. d.CONH*).
*Removable in D₂O.

NH₂OH assay: = 96% Biochromatography: 1 zone at R_f = 0.31

EXAMPLE 4

D-α-[DL-β-(-p-Nitrophenyl)-α-ureidopropionamido]-(-p-hydroxyphenyl)acetamidopenicillanic acid.

(R = p—HO—Ph; R¹ = p—NO₂—PhCH₂; R³ = H; R² = NHCONH₂; M=H; α¹ = DL).

Prepared by method Bii), from DL-β-(-p-Nitrophenyl)-α-ureidopropionic acid and amoxycillin.

Yield: 60%. νmax (KBr): 3350, 1770, 1650, 1514 and 1230 cm⁻¹. δ[(CD₃)₂SO]: 1.42 (3H. s. gem methyl); 1.55 (3H. s. gem methyl); 3.0 (2H. m. CH₂CH<); 4.05 (1H. s. C-3 proton); ~4.60 (1H. m. -CH₂CH<); 5.25 - 5.80

(5H. m. β-lactams,

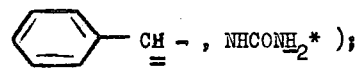

6.2 (1H. m. NHCONH₂*); 6.5 - 8.2 (8H. m. aromatics); 8.50, 9.00 (2 × 1H.m.CONH*).
*Removable in D₂O.

NH₂OH assay: 86.5% Biochromatography: 1 zone at R_f = 0.44

EXAMPLE 5

Sodium D-α-[DL-γ-Methylthio-α-ureidobutyramido]-phenylacetamidopenicillanate.

(R = Ph; R¹ = CH₃S (CH₂)₂-; R³=H; R² = NHCONH₂; M=Na; α¹ = DL).

Prepared by Method B, from N-Carbamoyl-DL-methionine and ampicillin, isolated as the sodium salt after treatment with sodium 2-ethylhexoate.

Yield: 51%. νmax (KBr): 3320 (broad), 1775, 1650, 1530, 1310, 1230 and 702cm⁻¹. δ[(CD₃)₂SO]: 1.48 (3H. s. gem methyl); 1.58 (3H. s. gem methyl); 1.4 - 2.2 (2H. m. -SCH₂CH₂CH<); 2.05 (3H. d. MeS-); 2.3 - 2.7 (2H. m. SCH₂—); 4.24 (1H. s. C-3 proton); 4.1 - 4.6 (1H. m. SCH₂CH₂CH<); 5.2 - 5.9 (5H. m. β-lactams. PhCH< and —COHN₂*); 6.4 (1H. m. CONH*-); 7.40 (5H. m. aromatics); 8.60 and 9.00 (2 × 1H. d. CONH*-).
* Removable in D₂O.

NH₂OH assay: 93.8% Biochromatography: 1 zone at R_f = 0.36.

EXAMPLE 6

Sodium D-α-[DL-γ-Methylthio-α-ureidobutyramido](p-hydroxyphenyl)acetamido penicillanate.

(R = p-HO-Ph; R¹ = CH₃S (CH₂)₂; R³ = H; R² = NHCONH₂; M=Na; α¹=DL).

Prepared by method Bii), from M-Carbamoyl-DL-methanionine and amoxycillin, isolated as the sodium salt after treatment with sodium 2-ethylhexoate.

Yield: 43%. νmax (KBr): 3350 (broad), 1770, 1650, 1510, 1235cm⁻¹. δ[(CD₃)₂SO]: 1.45 (3H. s. gem methyl); 1.57 (3H. s. gem methyl); 1.4 - 2.2 (2H. m. -SCH₂CH₂CH<); 2.05 (3H. d. MeS-); 2.3 - 2.7 (2H. m. SCH₂-); 4.24 (1H. s. C-3 proton); 4.1 - 4.6 (1H. m. SCH₂CH₂CH<); 5.2 - 5.9 (5H.m.β-lactams, PH CH< and CONH₂*); 6.4 (1H. m. CONH*-); 6.3 - 7.34 (4H. m. aromatics); 8.60 and 8.90 (2 × 1H.d.CONH*—).
* Removable in D₂O.

NH₂OH assay: 85.5% Biochromatography: 1 zone at R_f = 0.29.

EXAMPLE 7

Sodium D-α-[DL-α-formamido-γ-methylthiobutyramido]-phenylacetamido pencillanate (R = Ph; R¹ = CH₃S (CH₂)₂; R³ = H; R² = NHCHO; M=Na; α¹ = DL).

Prepared by Method B, using N-Formyl-DL-methionine and ampicillin, isolated as the sodium salt after treatment with sodium 2-ethyl hexoate.

Yield: 63%. νmax (KBr): 3300 (broad), 1780, 1732, 1645, 1525, 1302, 1225 and 700 cm⁻¹ δ[(CD₃)₂SO]: 1.46 (3H. s. gem methyl); 1.55 (3H. s. gem methyl); 1.7 - 2.2 (2H. m. CH₃SCH₂CH₂C$\underline{H}$<); 2.05 (3H. d. CH₃S-); 2.3 - 2.7 (2H. m. CH₃S C$\underline{H}_2$CH₂); 4.23 (1H. s. C-3 proton); 4.70 (1H. m. -C$\underline{H}^1$ NHCHO); 5.3 - 5.9 (3H. m. β-lactams and PhC$\underline{H}$<); 7.37 (5H. m. aromatics); 8.08 (1H. s. NHC$\underline{H}$O); 8.31, 8.60 and 9.00 (3 × 1H. d. -COH$\underline{N}$-*).
* Removable in D₂O.

NH₂OH assay: 100% Biochromatogram: Single zone at R$_f$ = 0.40.

EXAMPLE 8

D-α-[DL-β-(p-Chlorophenyl)-α-ureidopropionamido]-(p-hydroxyphenyl)acetamidopenicillanic acid.

(R = p-HO-Ph; R¹ = p-Cl-PhCH₂; R³ = H; R² = NHCONH₂; M=Na; α¹ = DL).

Prepared by Method Bii from DL-β-(P-Chlorophenyl)-α-ureidopropionic acid and amoxycillin.

Yield: 45%. νmax (KBr): 3360, 1770, 1650, 1514 and 1230 cm⁻¹. δ[(CD₃)₂SO]: 1.42 (3H. s. gem dimethyl); 1.58 (3H. s. gem dimethyl); 2.86 (2H. m. -C$\underline{H}_2$CH<); 4.26 (1H. s. C-3 proton); 4.55 (1H. m. -C$\underline{H}_2$C$\underline{H}$<);

5.58 (5H. m. β-lactams,

6.24 (1H. m. N$\underline{H}$CONH₂*); 6.78 and

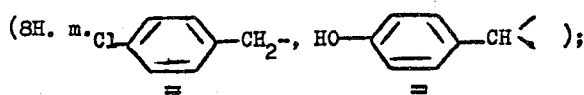

8.53 (1H. m. CON$\underline{H}$); 9.04 (1H. m. CON$\underline{H}$).
* Removable in D₂O.

Biochromatagraphy: R$_f$ = 0.42 Analysis: C₂₆H₂₈N₅O₇SCl required: C, 52.93; H, 4.75; N, 11.87; S, 5.43; Cl, 6.02. Found: C, (50.23); H, 4.79; N, 11.13; S, 5.32; Cl, 5.97.

EXAMPLE 9

D-α-[DL-β-(p-Fluorophenyl)-α-ureidopropionamido]-phenylacetamido penicillanic acid (R = Ph; R¹ = p-F-PhCH₂; R³ = H; R² = NHCONH₂; M = H; α¹ = DL)

Prepared by method B from DL-β-(p-fluorophenyl)-α-ureidopropionic acid and ampicillin.

Yield: 42%. νmax (KBr): 3360, 1773, 1651, 1510, 1226 and 720 cm⁻¹. δ[(CD₃)₂SO]: 1.42 (3H. s. gem methyl); 1.57 (3H. s. gem methyl); 1.57 (3H. s. gem methyl); 2.87 (2H. m. C$\underline{H}_2$CH<); 4.24 (1H. s. C-3 proton); 4.56 (1H. m. C$\underline{H}_2$C$\underline{H}$<); 5.65 (5H. m. β-lactams, α-proton, -NHCON$\underline{H}_2$*), 6.27 (1H. d. NHCONH₂*); 7.24 (9H. m. P$\underline{h}$ CH<);

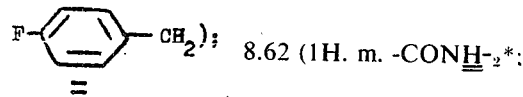 8.62 (1H. m. -CON$\underline{H}$-₂*:

9.17 (1H. m. CON$\underline{H}$*).
* Removable in D₂O.

Bichromatography: 1 Spot at R$_f$ = 0.42.

EXAMPLE 10

D-α-[DL-β-(p-Chlorophenyl)-α-ureidopropionamido]phenylacetamido penicillanic acid (R = Ph; R¹ = p-Cl-PhCH₂; R³ = H: R² = NHCONH₂; M=N; α¹ = DL).

Prepared by Method B, from DL-β-(p-chlorophenyl)-α-ureidopropionic acid.

Yield: 38% νmax (KBr): 3360, 1770, 1650, 1514 and 1230 cm⁻¹. δ[(CD₃)₂SO]: 1.40 (3H. s. ge m methyl); 1.56 (3H. s. gem methyl); 2.85 (2H. m. —CH₂CH<); 4.25 (1H. s. C-3 proton); 4.55 (1H. m. -CH₂C$\underline{H}$<);

5.58 (5H. m. β-lactams,

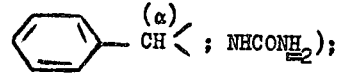

6.25 (1H. m. NCONH₂); 7.30 (9H. m. aromatic protons); 8.53 (1H. m. CONH); 9.00 (1H. m. CONH). NH₂OH Assay: 94% Biochromatography: 1 zone at R$_f$ = 0.59.

EXAMPLE 11

Sodium D-α-[DL-β-(p-Nitrophenyl)-α-ureidopropionamido]-phenylacetamidopenicillanate.

(R = Ph; R¹ = p-NO₂-PhCH₂; R³ = H; R² = NHCONH₂; M=Na; α¹ = DL).

Prepared by method B, from DL-β-(p-Nitrophenyl)-α-ureidopropionic acid and ampicillin; isolated as the sodium salt by treatment with sodium 2-ethylhexoate.

Yield: 55%. νmax (KBr); 3350, 1770, 1650, 1514 and 1230 cm⁻¹. δ[(CD₃)₂SO]: 1.42 (3H. s. gem methyl); 1.60 (3H. s. gem methyl); 3.0 (2H. m. -C$\underline{H}_2$CH<); 4.20 (1H. s. C-3 proton); 4.7 (1H. m. -CH₂C$\underline{H}$<); 5.3–5.85

(5H.m. β-lactams,

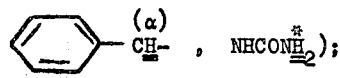

6.2 (1H. m. NHCONH₂*); 7.18 - 8.25 (9H. m. aromatics); 8.50, 9.05 (2 × 1H. m. CONH*).
* Removable in D₂O.

NH₂OH assay: 93.9% Bichromatography: 1 zone at R$_f$ = 0.5.

EXAMPLE 12

D-α-(D-p-Phenyl-α-ureidopropionamido)-(p-hydroxyphenyl)acetamidopenicillanic acid (R = p-HO-Ph; R¹ = PhCH₂; R³ = H; R² = NHCONH₂; M=H; α¹ = D).

Prepared by method Biii, using D-β-phenyl-α-ureidopropionic acid and amoxycillin.

Yield: 63% M.P. 235°–238°C. νmax (KBr): 3360 (broad), 1740, 1650, 1520 and 1230 cm⁻¹. δ[(CD₃)₂SO]: 1.47 (3H. s. gem methyl); 1.60 (3H. s. gem methyl); 2.95 (2H. m. Ph.C$\underline{H}_2$.CH<); 4.27 (1H. s. C-3 proton); 4.60 (1H. m. PhCH₂C$\underline{H}$<); 5.30–5.80;

(5H. m. β-lactams, ureido-N$\underline{H}_2$*,

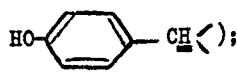);

6.20 (1H. d. ureido-N$\underline{H}$-*); 6.70–7.35;

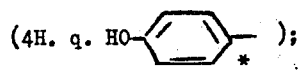;

7.25 (5H. s. benzyl aromatics), 8.50 (1H. d. -CON$\underline{H}$-*); 9.00 (1H. d. -CON$\underline{H}$-*).
* Removable in D₂O.

Hydroxylamine Assay: 107.7%. Biochromatography: One zone at $R_f$ = 0.35. Analysis for $C_{26}H_{29}N_5O_7S$; Required (%) C, 56.22; H, 5.23; N, 12.61; S, 5.77. Found (%) C, (55.33); H, 5.44; N, 11.99; S, 5.44.

EXAMPLE 13

D-α-(DL-α-acetamido-β-phenylpropionamido)-phenyl-acetamido-penicillanic acid (R = Ph; R¹ = PhCH₂; R³ = H; R² = NHCOCH₃; M = H; α¹ = DL)

Prepared by method Bi, from DL-α-acetamido-β-phenylpropionic acid and ampicillin.

Yield: 94%. νmax (KBr): 33.60 (broad) 1774, 1648, 1511, 1215 and 701cm⁻¹. δ[(CD₃)₂SO]: 1.43 (3H. s. gem methyl); 1.56 (3H. s. gem methyl); 1.77 (3H. s. NHCOC$\underline{H}_3$); 2.7–3.2 (2H.m. PhC$\underline{H}_2$CH<) 4.24 (1H.s. C-3 proton); 4.6–4.9 (1H.m. PhCH₂C$\underline{H}$<); 5.62 (3H.m. β-lactams, PhC$\underline{H}$<); 7.38 (10H.m. P$\underline{h}$CH<; P$\underline{h}$ CH₂OH<); 8.0–9.3 (3H.m. removable in D₂O, -COH$\underline{N}$-) Hydroxyalamine Assay: 62.1%. Biochromatography: 1 zone at $R_f$ = 0.26. Analysis: $C_{27}H_{30}N_4O_6S$ required: C, 60.22; H, 5.58; N, 10.41; S, 5.95. Found: C, (57.45); H, 5.69; N, 9.98; S, 6.03.

EXAMPLE 14

D-α-[DL-α-(3-Methylureido)-β-phenyl-propionamido]-phenylacetamido penicillanic acid (R = Ph; R¹ = PhCH₂; R³ = NHCONHCH₃; M = H; α¹ = DL)

Prepared by method Bi, starting from DL-α-(3-methylureido)-β-phenylpropionic acid ampicillin.

Yield: 75%. νmax (KBr): 1775, 1637, 1560, 1490, 1297, 1219 and 702cm⁻¹. δ[(CD₃)₂SO]: 1.45 (3H.s. gem methyl); 1.57 (3H.s. gem methyl); 2.52 (3H.s. NHCONHC$\underline{H}_3$); 2.90 (2H.m. PhC$\underline{H}_2$CH<); 4.27 (1H.s. C-3 proton); 4.63 (1H.m. PhCH₂C$\underline{H}$<); 5.64 (3H.m. β-lactams, PhC$\underline{H}$<); 7.32 (10H.m. P$\underline{h}$CH₂CH<; P$\underline{h}$CH<); 8.63 (1H.m. removable in D₂O,—CON$\underline{H}$—); 9.18 (1H.m removable in D₂O,—CON$\underline{H}$—); ca 6.25 (broad signal due to —N$\underline{H}$ CON$\underline{H}$—).

Biochromatography: 1 zone at $R_f$ = 0.47 Analysis: $C_{27}H_{31}N_5O_6S$ required: C, 58.48, H, 5.60; N, 12.64; S, 5.78 Found: C, (56.78); H, 5.59; N, 12.73; S, 5.05.

EXAMPLE 15

D-α-[DL-β-(-p-Fluorophenyl)-α-ureido-propionamido]-(-p-hydroxyphenyl)acetamido-penicillanic acid (R = -p-HO-Ph; R¹ = -p-F-PhCH₂; R³ = H; R² = NHCONH₂; M = H, α¹ = DL)

Prepared by method Bii, from DL-β-(-p-fluorophenyl)α-ureidopropionic acid and amoxycillin.

Yield: 48% νmax (KBr): 3360, 1764, 1650, 1510, 1224, and 838cm⁻¹ δ[(CD₃)₂SO]: 1.43 (3H.s. gem methyl); 1.54 (3H.s. gem methyl); 2.88 (2H.m. -C$\underline{H}_2$CH<); 4.14 (1H.s. C-3 proton); 4.2–4.8 (1H.m. CH₂CH<); 5.3–7.5 (extremely strong signals containing β-lactams,

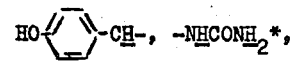

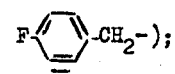

$\delta$ = 8.3–9.2 (2H.m.-CON$\underline{H}$*)
* removable in D₂O

Hydroxylamine Assay: 84.7%. Biochromatography 1 zone at $R_f$ = 0.41.

EXAMPLE 16

D-α-[D-β-Phenyl-α-(n-valeramido)-propionamido]-phenylacetamido penicillanic acid (R = Ph; R¹ = PhCH₂; R³ = H; R² = NHCO(CH₂)₃CH₃; M = H; α¹ = D)

Prepared by method Bi, from N-valeroyl-D-β-phenylalanine

Yield: 19% νmax (KBr): 3290 (br), 1773, 1635, 1525, 1300, 1224, 733, 702cm⁻¹. δ[(CD₃)SO]; 0.82 (3H.m. (CH₂)₃CH₃), 1.0–1.7 (4H.m. CH₂C$\underline{H}_2$C$\underline{H}_2$CH₃) 1.45 (3H.s. gem methyl); 1.58 (3H.s. gem methyl); 2.09 (2H.m. C$\underline{H}_2$(CH₂)₂CH₃), 3.00 (2H.m. PhC$\underline{H}_2$), 4.28 (1H.s. C-3 proton), 4.78 (1H.m. PhC$\underline{H}_2$C$\underline{H}$<) 5.4–5.9 (3H.m. β-lactams and PhC$\underline{H}$<), 7.2–7.5 (10H.m. aromatic protons), 8.05 (1H.d. —CON$\underline{H}$—), 8.47 (1H.m. CON$\underline{H}$), 9.13 (1H.m. —CON$\underline{H}$—). NH₂OH Assay: 90%. Biochromatography: Single zone $R_f$ = 0.70. Analysis: Found: C, 60.96; H, 6.05; N, 9.46; S, 5.65% $C_{30}H_{36}N_4O_6S$ requires C, 62.10; H, 6.21; N, 9.66; S, 5.52.

EXAMPLE 17

D-α-[D-β-Phenyl-α-pivaloylaminopropionamido]-phenylacetamido penicillanic acid (R = Ph; R¹ = PhCH₂; R³ = H; R² = -NHCOC(CH₃)₃; M = H; α¹ = D)

Prepared by method Bi, from α-t-Butyramido-D-β-phenyl propionic acid.

Yield: 6% νmax (KBr); 3350(br), 1772, 1639, 1517, 1300, 1212, 702cm⁻¹. δ[(CD₃)₂SO]: 0.97 (9H.s. (CH₃)₃), 1.39 (3H.s gem methyl), 1.52 (3H.s. gem methyl), 2.97 (2H.m. PhC$\underline{H}_2$), 4.20 (1H.s. C-3 proton), 5.35–5.85 (4H.m. β-lactams and PhC$\underline{H}$<), 4.65 (1H.m. PhCH$_2$C$\underline{H}$<), 7.25 (5H.s. phenyl protons), 7.39 (5H.m. phenyl protons), 7.2-7.6 (1H.m. —NHCO—*), 8.50 (1H.d. —NHCO—*), 9.27 (1H.d. —N$\underline{H}$—CO—).
* removed by D$_2$O.

NH$_2$OH Assay: 102%. Biochromatography: 0.71.

EXAMPLE 18

D-α-[D,L-α-Benzamido-β-phenylpropionamido]-phenylacetamido penicillanic acid (R = Ph; R$^1$ = PhCH$_2$; R$^3$ = H; R$^2$ = NHCO Ph; M = H; α$^1$ = D,L)

Prepared by method Bi, from α-Benzamido-D,L-β-phenylpropionic acid.

Yield: 22%. νmax (KBr): 3300, 1775, 1635, 1522, 1302, 122, 702cm$^{-1}$. δ[(CD$_3$)$_2$SO]: 1.42 (3H.s. gem methyl), 1.57 (3H.s. gem methyl) 3.11 (2H.m. PhC$\underline{H}_2$), 4.24 (1H.s. C-3 proton), 5.00 (1H.m. PhCH$_2$C$\underline{H}$<), 5.4–5.9 (3H.m. β-lactams and PhC$\underline{H}$<), 7.2–8.0 (10H.m. aromatic protons), 8.65, 8.80 and 9.20 (3 × 1H.d. -N$\underline{H}$CO-*).
* removed in D$_2$O.

NH$_2$OH Assay: 88%. Biochromatography: Single zone 0.70.

EXAMPLE 19

D-α-[D,L-γ-Phenyl-α-ureidobutyramido]-p-hydroxyphenylacetamido penicillanic acid (R = p HO-Ph; R$^1$ = PhCH$_2$CH$_2$-; R$^3$ = H; R$^2$ = -NHCONH$_2$ M = H; α$^1$ = D,L)

Prepared by method Biii, from α-ureido-D,L-α-phenylbutyric acid.

Yield: 35%. νmax (KBr): 3315(br), 1770, 1650, 1510, 1454, 1227, 842, 703cm$^{-1}$. δ[(CD$_3$)$_2$SO]: 1.42 (3H.s. gem methyl), 1.52 (3H.s. gem methyl), 2.00 (2H.m. PhC$\underline{H}_2$CH$_2$), 2.52 (2H.m. PhCH$_2$C$\underline{H}_2$), 4.1–4.4 (1H.m. PhCH$_2$CH$_2$C$\underline{H}$<), 4.25 (1H.s. C-3 proton), 5.3-5.8 (3H.m. β-lactams and PhC$\underline{H}$<), 7.25 (9H.m. aromatic protons, 6.34, 6.73 (2 × 1H.d. N$\underline{H}$CO*), 8.32–9.10 (3H.m. —CON$\underline{H}$—* and —CON$\underline{H}$*$_2$)
* removed by D$_2$O NH$_2$OH Assay: 80%. Biochromatography: R$_f$ 0.5.

EXAMPLE 20

D-α-[D,L-α-Formamido-β-phenylpropionamido]-phenylacetamido penicillanic acid (R = Ph; R$^1$ = PhCH$_2$; R$^3$ = H; R$^2$ = -NHCHO; M = H; α$^1$ = D,L)

Prepared by method Bi from N-Formyl-D,L-phenylalanine.

YIELD: 55%. νmax (KBr): 3242(br), 1771, 1638, 1522, 1379, 1300, 1226, 731, 701cm$^{-1}$. δ[(CD$_3$)$_2$SO]: 1.46 (3H.s. gem methyl), 1.59 (3H.s. gem methyl); 2.88 (2H.m. PhC$\underline{H}_2$CH<), 4.21 (1H.s. C-3 proton), 4.83 (1H.m. PhCH$_2$C$\underline{H}$<), 5.4–5.9 (3H.m. β-lactams and PhC$\underline{H}$<), 7.2–7.6 (10H.m. aromatic protons), 7.97 (1H.s. C$\underline{H}$O), 2.27, 2.70 and 9.11 (3 × 1H.d. —N$\underline{H}$-CO*—).
* removed by D$_2$O.

NH$_2$OH Assay: 79%. Biochromatography: Single zone R$_f$ 0.52.

EXAMPLE 21

D-α-[D-β-Phenyl-α-propionamido-propionamido]-phenylacetamido penicillanic acid (R = Ph; R$^1$ = PhCH$_2$; R$^3$ = H; R$^2$ = NHCOCH$_2$CH$_3$; M = H; α$^1$ = D)

Prepared by method Bi from α-Propionamido-D-β-phenylpropionic acid.

Yield: 13%. νmax (KBr); 3229(br), 1770, 1637, 1524, 1226, 702cm$^{-1}$. δ[(CD$_3$)$_2$SO]: 0.89 (3H.t. COCH$_2$C$\underline{H}_3$), 1.42 (3H.s. gem methyl), 1.60 (3H.s. gem methyl), 1.98 (2H.m. -NHC$\underline{H}_2$CH$_3$), 2.90 (2H.m. PhC$\underline{H}_2$CH<), 4.21 (1H.s. C-3 proton), 4.70 (1H.m. PhCH$_2$C$\underline{H}$<), 5.4–5.9 (3H.m. β-lactams and PhC$\underline{H}$<), 7.2–7.6 (10H.m. aromatic protons), 8.01, 8.42 and 9.10 (3 × 1H.d. —CON$\underline{H}$*—).
* removed by D$_2$O.

NH$_2$OH Assay: 75%. Biochromatography: Single zone R$_f$ 0.58.

EXAMPLE 22

D-α-[D-α-Isobutyramido-β-phenylpropionamido]-phenylacetamido penicillanic acid (R = Ph; R$^1$ = PhCH$_2$-; R$^3$ = H; R$^2$ = NHCOCH(CH$_3$)$_2$; M = H; α$^1$ = D).

Prepared by method Bi, from α-isobutyramido-D-β-phenyl propionic acid

Yield: 18% νmax (KBr): 3300(br), 1771, 1638, 1526, 1300, 1222, 702cm$^{-1}$. δ[(CD$_3$)$_2$SO]: 0.85 (6H.t. CH(C$\underline{H}_3$)$_2$, 1.41 (3H.s. gem methyl), 1.56 (3H.s. gem methyl), 2.97 (2H.m. PhC$\underline{H}_2$CH<), 4.25 (1H.s. C-3 proton), 4.70 (2H.m. C$\underline{H}$(CH$_3$)$_2$ and PhCH$_2$C$\underline{H}$<), 5.4–5.9 (3H.m. β-lactams and PhC$\underline{H}$<), 7.1–7.6 (10H.m. aromatic protons), 7.97, 8.47 and 9.13 (3 × 1H.d. —N$\underline{H}$CO—*).
* removed by D$_2$O NH$_2$OH Assay: 103% Biochromatography: Single zone R$_f$ 0.66

EXAMPLE 23

D-α-[D-γ-Methylthio-α-ureidobutyramido]-phenylacetamido penicillanic acid (R = Ph; R$^1$ = CH$_3$S(CH$_2$)$_2$-; R$^3$ = H; R$^2$ = -NHCONH$_2$; M = H; α$^1$ = D)

Prepared by method Fi, from N-Carbamoyl-D-methionine.

Yield: 43%. νmax (KBr): 3320(br), 1775, 1650, 1530, 1310, 1230, and 702cm$^{-1}$. δ[(CD$_3$)$_2$SO]: 1.48 (3H.s. gem methyl), 1.61 (3H.s. gem methyl), 1.4–2.2 (2H.m. -SCH$_2$C$\underline{H}_2$CH<), 2.1 (3H.s.CH$_3$S—), 2.3–2.7 (2H.m. —SC$\underline{H}_2$CH$_2$CH) 5.2–5.9 (5H.m.β-lactams, PhCH and —CONH$_2$*) 6.4 (1H.m. —CON$\underline{H}$—*)
* removed by D$_2$O.

NH$_2$OH Assay: 98%. Biochromatography: Single zone R$_f$ 0.34. Analysis: Found: C, 49.33; H, 5.64; N, 12.94; S, 11.59% C$_{22}$H$_{29}$N$_5$O$_6$S$_2$ requires C, 50.48; H, 5.54; N, 13.38; S, 12.24%.

EXAMPLE 24

D-α-[D,L-α-Methyl-α-ureidovaleramido]-phenylacetamido penicillanic acid (R = Ph; R$^1$ = (CH$_3$)$_2$CHCH$_2$-; R$^3$ = H; R$^2$ = —NHCONH$_2$; M = H; α$^1$ = D,L)

Prepared by method B from α-methyl-D,L-α-ureido valeric acid.

Yield: 36% νmax (KBr) 3325(br), 1775, 1723, 1650, 1530, 1310, 1222, 702cm$^{-1}$ δ[(CD$_3$)$_2$SO]: 0.84 and 0.95 (2 × 3H.s. CH(C$\underline{H}_3$)$_2$), 1.45 (3H.s. gem methyl), 1.61 (3H.s. gem methyl), 0.78–2.0 (3H.m. CH$_2$CH(CH$_3$)$_2$), 4.25 (1H.s. C-3 proton), 4.0–4.6 (1H.m. —C$\underline{H}$NHCONH$_2$), 5.3–5.9 (5H.m. β-lactams, PhC$\underline{H}$< and CONH$_2$*), 6.2 (1H.d. —CON$\underline{H}$—), 7.2–7.6 (5H.m. aromatic protons), 8.48 and 9.04 (2 × 1H.d. —CO—N$\underline{H}$—* )

* removed by D$_2$O.

NH$_2$OH Assay: 79%. Biochromatography: Single zone R$_f$ 0.44.

EXAMPLE 25

D-α-[D,L-α-Formamido-β-(p-hydroxyphenyl) propionamido]phenylacetamido penicillanic acid.

(R=Ph; R'=pHO-PhCH$_2$–; R$^3$ = H; R$^2$=NHCHO; M=H; α'=D,L)

Prepared by method B from N-Formyl-D,L-Tyrosine

Yield: 23%. νmax (KBr): 3290 (br.), 1773, 1735, 1650, 1518, 1378, 1230 and 701cm$^{-1}$. δ[(CD$_3$)$_2$SO] 1.45 (3H.s gem methyl), 1.62 (3H.s. gem methyl), 2.7–3.2 (2H.m. PhC$\underline{H}_2$—), 4.24 (1H.s. C3 proton), 4.8 (1H.m. -C$\underline{H}$NHCHO), 5.35–5.96 (3H.m. βLactams and Ph C$\underline{H}$), 6.7 and 7.0 (2 × 2H.m. pHO—C$_6\underline{H}_4$—), 7.36 (5H.m. Aromatic protons), 7.92 (1H.s—NH-CHO), 8.2 (1H.d. — CON$\underline{H}$—*) 8.7 and 9.12 (2 × 1H.m.—CON$\underline{H}$—*).

* removed by D$_2$O.

NH$_2$OH Assay: 105%. Biochromatogram: Single Zone R$_f$ 0.39.

EXAMPLE 26

Dα-[D-α-Formamido -γ-methylthiobutyramido]-phenylacetamido penicillanic acid.

(R=Ph; R'=CH$_3$S (CH$_2$)$_2$–; R$^3$=H; R$^2$=NHCHO; M=H; α'=D)

Prepared by method Fii from N -Formyl-D-methionine.

Yield: 5.8% νmax (KBr): 3300 (br), 1780, 1732, 1645, 1525, 1302, 1225, 700 cm$^{-1}$. δ[(CD$_3$)$_2$SO]: 1.46 (3H.s. gem methyl), 1.55 (3H.s. gem methyl), 1.7-22 (2H.m. CH$_3$SCH$_2$CH$_2$CH<), 2.0 (s. 15–17% of L-C$\underline{H}_3$ SCH$_2$CH$_2$CH<) 2.1 (S. 83–5% of D-C$\underline{H}_3$SCH$_2$CH$_2$CH<), 2.3–2.7 (2H.m. CH$_3$SC$\underline{H}_2$CH$_2$CH$_2$), 4.23 (1H.s. C$_3$ proton), 4.70 (1H.m. -C$\underline{H}$NHCHO), 5.3–5.9 (3H.m. β lactams, and PhC$\underline{H}$<), 7.37 (5H.m. aromatic protons), 8.08 (1H.s. -NH-C$\underline{H}$O), 8.31, 8.59 and 9.02 (3 × 1H.s. -CON$\underline{H}$-)

* removed by D$_2$O.

NH$_2$OH Assay: 102%. Biochromatogram: Single zone R$_f$ 0.41.

EXAMPLE 27

D-α-[D-γ-Methyl-α-ureidovaleramide]-phenylacetamido penicillanic acid.

(R=Ph; R'= (CH$_3$)$_2$ CHCH$_2$; R$^3$=H; R$^2$=NHCONH$_2$; M=H; α'=D). Prepared by method Fi from γ-methyl-D hα-ureido valeric acid.

Yield: 28% M.p: 168°–170°C (Decomp.). νmax (KBr): 3315 (br.), 1775, 1730, 1650, 1530, 1310, 1220, 700 cm$^{-1}$. δ[(CD$_3$)$_2$SO]: 0.85 and 0.92 (6H.d. CH(C$\underline{H}_3$)$_2$), 1.50 (3H.s. gem methyl) 1.66 (3H.s. gem methyl), 0.8–2.0 (3H.m. C$\underline{H}_2$C$\underline{H}$ (CH$_3$)$_2$), 4.28 (1H.s. C3 proton), 4.1–4.5 (1H.m. C$\underline{H}$ NHCONH$_2$), 5.3–5.9 (5H.m.β lactams PhC$\underline{H}$<and CON$\underline{H}_2$*), 6.22 (1H.d.—CONH*—), 7.36 (5H.m. aromatic protons), 9.07 and 9.40 (2 × 1H.d.— CO N$\underline{H}$*—)

* removed by D$_2$O.

NH$_2$OH Assay: 95%. Biochromatogram: Single zone R$_f$ 0.45 Analysis: Found: C, 54.71; H, 6.15; N, 13.78; S, 6,49%. C$_{23}$H$_{31}$N$_5$O$_6$S requires C, 54.65, H, 6.14; N, 13.86; S, 6.34%.

EXAMPLE 28

D-α[L-γ-Methylthio-α-ureidobutyramido] phenylacetamido penicillanic acid (R=Ph; R'= (CH$_3$) S (CH$_2$)$_2$—; R$^3$=H; R$^2$= NHCONH$_2$; M=H, α'=L).

Prepared by method Fi from N-Carbamoyl-L-methionine.

Yield: 19% M.p.: 163°–6°C (Decomp.). νmax (KBr): 3350 (br), 1775, 1650, 1522, 1305, 1220, 702 cm$^{-1}$. δ[(CD$_3$)$_2$SO]: 1.46 (3H.s gem methyl), 1.60 (3H.s. gem methyl) 1.5–2.2 (2H.m. CH$_3$CH$_2$C$\underline{H}_2$CH<), 2.00 (3H.s. CH$_3$S) 2.2–2.6 (2H.m. CH$_3$ SC$\underline{H}_2$CH$_2$CH), 4.27 (1H.s. C3 proton), 1.38 (1H.m. CH$_3$CH$_2$CH$_2$CH<), 5.60 5H.m.

β lactams, PhC$\underline{H}$<, —CON$\underline{H}$*$_2$), 7.39 (5H.m. aromatic protons), 6.34 (1H.m. —C$\underline{H}$CONH*$_2$), 9.12 and 9.48 (2 × 1H.d —CONH*—)

*removed by D$_2$O

NH$_2$OH Assay: 100% Biochromatogram: Single zone R$_f$ 0.38 Analysis: Found: C, 49.64; H, 5.98; N, 13.08; S, 11.72%. C$_{22}$H$_{29}$N$_5$O$_6$S$_2$ requires C 50.48; H, 5.54; N, 13.38; S, 12.24%.

EXAMPLE 29

Triethylammonium D-α-[D-β-(3-Indolyl)-α-ureido-propionamido] phenylacetamido penicillanate.

(R=Ph; R' = [3-indolylmethyl group]; R$^3$=H; R$^2$=NHCONH$_2$; M=HN (CH$_2$CH$_3$)$_3$; α'=D.

Prepared by method Fiii)

from N-Carbamonyl-D-Tryptophan

Yield: 52% M.p.: 200–3°C (Decomp). νmax (KBr): 3350 (br), 1767, 1660, 1640, 1610, 1530, 1458, 1392, 749 cm$^{-1}$. δ[(CD$_3$)$_2$SO]: 1.11 (3H.t. OCH$_2$C$\underline{H}_3$), 1.42 (3H.s. gem methyl), 1.53 (3H.s. gem methyl), 2.7–3.2 (4H.m.—C$\underline{H}_2$CH<and OC$\underline{H}_2$CH$_3$), 4.00 (1H.s C$_3$ proton), 4.59 (1H.m. CH$_2$C$\underline{H}$<) 5.3–5.9 (5H.m. β lactams, PhC$\underline{H}$< and CON$\underline{H}$*$_2$), 6.9–7.7 (10H.m. aromatic protons), 6.29, 8.53 and 8.97 (3 × 1H.d. —NHC̲O*), 10.84 (1H.s. indolyl N$\underline{H}$*).

*removed by D$_2$O.

NH$_2$OH Assay: 94% Biochromatogram: single zone R$_f$ 0.30 Analysis: Found: C, 59.38; H, 6.65; N, 14.35; S, 4.60% C$_{34}$H$_{45}$N$_7$O$_6$S requires C, 60.07; H, 6.67; N, 14.42, S, 4.72%.

EXAMPLE 30

Triethylammonium D-α-[D,L-α-formamido-β-(3-indoly)-propionamido] phenylacetamido penicillinate, (R= Ph; R'=  ;

R³=H; R² = -NHCHO;M=HN (CH₂CH₃)₃; α'=D,L.

Prepared by method Fi)

from N-Formyl-D,L-tryptophan, the product crystallising on dilution with ether.

Yield: 50%. νmax (KBr): 3310 (br), 1772, 1770, 1665, 1530, 1458, 1388, 1218, 748 cm$^{-1}$. δ [(CD₃)SO]: 1.17 (3H.t.OCH₂C$\underline{H}$₃), 1.44 (3H.s gem methyl), 1.58 (3H.s. gem methyl), 2.8–3.3 (4H.m. OC$\underline{H}$₂CH₃ and C$\underline{H}$₂CH<), 4.12 (1H.s. C₃ proton), 4.90 (1H.m. CH₂C$\underline{H}$<), 5.3–5.9 (3H.m. β-lactams and Ph C$\underline{H}$<), 7.0–7.8 (11H.m. 10 aromatic protons and N$\underline{H}$CONH₂) 8.00 (1H.S. C$\underline{H}$O), 8.0–9.0 (4H.m. 2 ×—N$\underline{H}$CO* and —CON$\underline{H}$₂*), 10.80 (1H.s indolyl N$\underline{H}$*)
*removed by D₂O.

NH₂OH Assay: 183%. Biochromatogram: Single zone R$_f$ 0.36.

EXAMPLE 31:

Triethylammonium -α-[D-γ-carbamoyl-α-Ureido butyrylamido] phenylacetamido penicillanate.

(R = Ph; R' = H₂NCO (CH₂)₂-; R³=H; R² = -NHCONH₂; M=HN (CH₂CH₃)₃; α'=D.

Prepared by method Fi) from N-Carbamoyl-D-glutamine, the product crystallising on dilution with ether.

Yield: 77%. νmax (KBr): 3400 (br.), 1773, 1698, 1660, 1603, 1532, 1458, 1397, 1314, 1220, 703 cm$^{-1}$.

δ [(CD₃)₂SO]: 1.16 (3H.t.OCH₂C$\underline{H}$₃), 1.43 (3H.s. gem methyl), 1.54 (3H.s. gem methyl), 1.5–2.2 (4H.m. —C$\underline{H}$₂CH₂—), 4.1(1H.s.C3 proton), 4.88 (1H.m. C$\underline{H}$ CH₂CH₂), 5.3–5.8 (3H.m β-lactams and PhC$\underline{H}$<), 6.3 (1H.m.—N$\underline{H}$CO*—), 7.3–7.7 (6H.m. aromatic protons and —NHCO*—), 8.2–9.0 (5H.m. 2 × —CON$\underline{H}$*₂) and —CON$\underline{H}$*
*removed by D₂O NH₂OH Assay: 100%. Biochromatogram: Single zone R$_f$ 0.34

EXAMPLE 32.

D-α-[D,L-β-Phenyl-α-ureidopropionamido]-1,4-cyclohexadienylacetamidopenicillanic acid.

R= 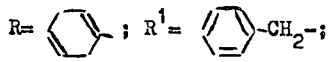

R³=H; R²=-NHCONH₂;M=H; α¹=D,L)

Prepared by method Bv from D,L-β-phenyl-α-ureidopropionic acid.

Yield: 65%. νmax (KBr): 3340, 1762, 1720, 1650, 1530, 1230 and 703 cm$^{-1}$. δ [(CD₃)₂SO]: 1.5(6H.d. gem dimethyls); 2.6(4H.s. cyclohexadiene methylenes); 2.6–3.2(2H.m. PhC$\underline{H}$₂CH<); 4.3(1H.s.C-3proton); 4.3–4.8(1H.m. PhCH₂C$\underline{H}$<);4.9–5.9

(5H.m.β-lactams, 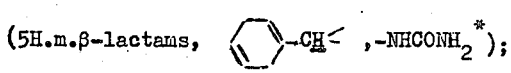

5.67(3H.s. cyclohexadiene methines);6.3–6.7(1H.m. —N$\underline{H}$CONH₂*);7.25(5H.s.P$\underline{h}$CH₂CH<);8.0–8.3(1H.-m.—CON$\underline{H}$—*);
*Removable with D₂O Hydroxylamine Assay: 59%. Biochromatography: R$_f$ 0.56.

EXAMPLE 33

Sodium D-β-[D-β-Phenyl-β-ureidopropionamido]-1,4-cyclohexadienylacetamido penicillanate.

( R= 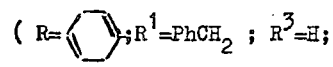;R¹=PhCH₂ ; R³=H;

R²=-NHCONH₂; M=Na; α¹=D)

Prepared by method Bvi from D-β-phenyl-α-ureidopropionic acid and epicillin.

Yield: 45%. γmax(KBr): 3350, 1760, 1630, 1530, 1230 and 703 cm$^{-1}$. δ [(CD₃)₂SO]: 1.53(6H.d. gem dimethyls); 2.65(4H.s.cyclohexadienyl methylenes); 2.8–3.0(2H.m.PhC$\underline{H}$₂—); 4.0(1H.s.C-3 proton); 4.2–4.7(1H.m.)CH₂C$\underline{H}$—); 5.0–5.6(5H.m.β-lactam protons HNC$\underline{H}$CO and HNCON$\underline{H}$₂):5.7(3H.s.cyclohexadienyl vinylic protons); 6.4–6.7(1H.m.—N$\underline{H}$-CONH₂); 7.25(5H.s.P$\underline{h}$); 8.0–9.0(2H.m.N$\underline{H}$) Hydroxylamine Assay: 76%. Biochromatography: 1 zone at R$_f$ 0.47

EXAMPLE 34

D-α-[DL-β-Benzyloxy-α-ureidopropionamido]-phenylacetamido-penicillanic acid.

(R=Ph; R¹=PhCH₂OCH₂; R³=H; R²=NHCONH₂; M=H; α¹=DL)

Prepared by method Bi from β-benzyloxy-α-ureido-DL-propionic acid and ampicillin.

Yield: 56%.

νmax (KBr): 3350, 1770, 1650, 1520, 1220 and 700 cm$^{-1}$ δ [(CD₃)₂SO]: 1.5(6H.d. gem dimethyls); 3.65(2H.m. —OC$\underline{H}$₂CHC<) 4.25(1H.s.C-3 proton); 4.5(3H.m. —OCH₂C$\underline{H}$< and PhC$\underline{H}$₂O—); 5.4–7.0(6H.m. β-lactam protons, HN-C$\underline{H}$CO and —NHCONH₂); 7.2–7.5(10H.m. 2 × phenyl aromatics); 8.5–9.2(2H.m. amide N$\underline{H}$'s)

Analysis: C₂₂H₃₁N₅O₇S.H₂O required: C, 55.3; H, 5.63; N, 11.9. Found : C, 56.03; H, 5.72: N, 11.46. Hydroxylamine Assay: 95%. Biochromatography: 1 zone at R$_f$ 0.42.

EXAMPLE 35

D-α-[DL-β-Benzyloxy-α-ureidopropionamido]-p-hydroxyphenylacetamido penicillanic acid.

(R = p-HO—Ph; R¹ = PhCH₂OCH₂; R³ = H; R² = —NHCONH₂; M = H; α¹ = DL)

Prepared by method Biii from DL-β-benzyloxy-α-ureidopropionic acid and amoxycillin.

Yield: 59%. νmax (KBr): 3350, 1775, 1725, 1650, 1515, 1230, and 703 cm$^{-1}$ δ [(CD₃)₂SO]: 1.5(6H.d. gem dimethyls); 3.5–3.9(2H.m. —OCH₂CH<); 4.23 (1H.s. C-3 proton); 4.3–4.7(3H.m. PhC$\underline{H}$₂O and OCH₂-C$\underline{H}$<); 5.2–5.9(5H.m. β-lactams, —HNC$\underline{H}$CO and CON$\underline{H}$₂) 6.2–6.5 (1H.m. —N$\underline{H}$CONH₂); 6.5–7.5(9H.m. aromatic protons) 8.3–9.0 (2H.m. amide N$\underline{H}$'s)

Hydroxylamine Assay: 84%. Biochromatography: 1 zone at R$_f$ 0.3.

EXAMPLE 36

D-α-[D-β-Phenyl-α-ureidopropionamido]-3-thienylacetamido penicillanic acid.

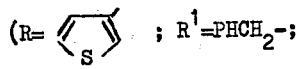

Prepared by method Biv from D-β-phenyl-α-ureidopropionic acid.

Yield: 59%. M.p. 175°-7°C (decomp.) νmax (KBr): 3360, 1750, 1650, 1525 and 704 cm⁻¹ δ [(CD₃)₂SO]: 1.53(6H.m. gem dimethyls); 2.92(2H.m. PhC$\underline{H}$₂CH<) 4.28(1H.s. C-3 proton); 4.61(1H.m. PhCH₂C$\underline{H}$<); 5.31–6.05 (5H.m. β-lactams, CON$\underline{H}$₂* and ThC$\underline{H}$<); 6.26(1H.d. CON$\underline{H}$—*); 7.37(8H.m. P$\underline{h}$ and T$\underline{h}$); 8.58 and 9.07 (2 × 1H.d. —CON$\underline{H}$—*)

*removed by D₂O

Hydroxylamine Assay: 100%. Biochromatogram: 1 zone at R_f 0.40

EXAMPLE 37

D-β-[D-α-Ureidopropionamido]-phenylacetamido penicillanic acid.

(R = Ph; R¹ = CH₃; R³ = H; R² = NHCONH₂; M = H; α¹ = D)

Prepared by method Bi from D-α-ureidopropionic acid.

Yield: 28%. M.p. 176°-8°C (decomp.) νmax(KBr): 3350 (br), 1773, 1720, 1635, 1530, 1234, and 700 cm⁻¹. δ [(CD₃)₂SO]: 1.21 (3H.d. C$\underline{H}$₃CHNH—); 1.43 (3H.s. gem dimethyls); 1.57 (3H.s. gem dimethyls); 4.26 (1H.s. C-3 proton); 4.33(1H.m. CH₃C$\underline{H}$NH—); 5.33–5.91(5H.m. β-lactams, PhC$\underline{H}$< and CON$\underline{H}$₂*); 5.91–6.54 (1H.m. —N$\underline{H}$CONH₂); 7.38(5H.m. aromatic protons); 8.47 and 9.05 (2 × 1H.d. —CON$\underline{H}$—*)

*removed by D₂O

Hydroxylamine Assay: 106%. Biochromatogram: 1 zone at R_f 0.21.

EXAMPLE 38

D-α-[D,L-β-Phenyl-α-ureido-propionamido]-phenylacetamido penicillanic acid (R = Ph; R¹ = PhCH₂; R³ = H; M = H; α¹ = D,L)

Prepared by method B from D,L-β-Phenyl-α-ureido propionic acid.

Yield: 37% νmax (KBr): 3350 (br.), 1775, 1650, 1525, 1225, 702 cm⁻¹. δ [(CD₃)₂SO]: 1.45 (3H.s. gem methyl), 1.57 (3H.s. gem methyl), 2.88 (2H.m. PhC$\underline{H}$₂—), 4.26 (1H.s. C3 proton), 4.60 (1H.m. PhCH₂C$\underline{H}$<), 5.33–5.94(5H.m. β-lactams, PhCH, —CON$\underline{H}$₂*), 6.24 (1H.d. —CON$\underline{H}$*—), 7.27 (10H.m. aromatic protons), 8.54 (1H.d. —CON$\underline{H}$*—), 9.11 (1H.d. —CON$\underline{H}$*—)

*removed by D₂O

NH₂OH Assay: 87% Biochromatogram: Single zone R_f 0.42.

EXAMPLE 39

D-α-[-α-Methyl-α-ureidopropionamido]-phenylacetamido penicillanic acid (R = Ph; R¹ = R³ = CH₃—; R² = NH₂CONH—; M = H)

Prepared by method B from α-Ureido-isobutyric acid

Yield: 6% νmax (KBr): 3400 (br.), 1785, 1715, 1650, 1535, 1225 and 700Cm⁻¹ δ[(CD₃)₂SO]: 1.38 (6H.s. (C$\underline{H}$₃)₂C<), 1.46 (3H.s. gem methyl) 1.57 (3H.s. gem methyl), 4.27 (1H.s. C3 proton), 5.37–5.88 (5H.m. β-lactams, CON$\underline{H}$₂*, Ph C$\underline{H}$<), 6.37 (1H.s. —N$\underline{H}$CO*—), 7.40 (5H.m. aromatic protons), 8.13 and 9.08 (2 × 1H.d. —CON$\underline{H}$*—)

* removed by D₂O

NH₂OH Assay: Biochromatogram: Single zone R_f 0.27. Analysis: Found: C, 52.60; H, 5.89; N, 14.34; S, 6.88% C₂₁H₂₇N₅O₆S required C, 52.82; H, 5.70; N, 14.67; S, 6.71%

EXAMPLE 40

D-α-[D,L-α-Methyl-β-phenyl-α-ureidopropionamido]-phenylacetamido penicillanic acid (R = Ph; R¹ = PhCH₂—; R³ = CH₃, R² = NHCONH₂, α = D,L)

Prepared by method B from D,L-α-Methyl-β-phenyl-α-ureidopropionic acid.

Yield: 43%. νmax (KBr): 3370 (br.), 1775, 1720, 1655, 1525, 1220 and 704 cm⁻¹. δ[(CD₃)₂SO]:

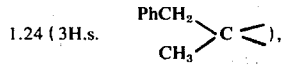

1.43 (3H.s. gem. methyl), 1.57 (3H.s. gem methyl), 2.80–3.70 (2H.m. PhC$\underline{H}$₂—), 4.30 (1H.m. C3 proton), 5.38–6.12 (5H.m. β-lactams, PhC$\underline{H}$ and CON$\underline{H}$₂*), 6.23 (1H.s. —CON$\underline{H}$—), 7.39 (10H.m. aromatic protons), 8.34 (1H.d. —CON$\underline{H}$—*), 9.28 (1H.d. —CON$\underline{H}$—*)

*removed by D₂O

Biochromatogram: Single zone R_f 0.54. Analysis: Found: C, 56.49; H, 5.66; N, 12.16% C₂₇H₃₁N₅O₆S requires C, 58.58; H, 5.64; N, 12.65%.

EXAMPLE 41

D-α-[D,L-α-Acetamido-β-phenylpropionamido]-p-hydroxyphenylacetamido penicillanic acid (R = p HO-Ph; R¹ = PhCH₂; R³ = H; R² = —NHCOCH₃; M = H; α¹ = D,L)

Prepared by method Bii from N-Acetyl-D,L-β-phenylalanine.

Yield: 40% νmax (Nujol): 3250 (br.), 1760, 1630, 1515, 1380, 1220, 710cm⁻¹. δ[(CD₃)₂SO]: 1.43 (3H.s. gem methyl), 1.57 (3H.s. gem methyl) 1.75 (3H.s. —NHCOC$\underline{H}$₃), 3.0 (2H.m. PhC$\underline{H}$₂), 4.24 (1H.s. C3 proton), 6.72 (1H.m. PhCH₂C$\underline{H}$<), 5.4–5.9 (3H.m. β-lactams and PhC$\underline{H}$<), 6.58–7.50 (9H.m. aromatic protons), 8.10, 8.47 and 8.95 (3 × 1H.m. —CON$\underline{H}$—*).

* removed by D₂O.

NH₂OH Assay: 105% Biochromatogram: Single zone R_f 0.51

EXAMPLE 42

D-α-[L-β-(p-Methoxyphenyl)-α-ureidopropionamide]phenylacetamido penicillanic acid (R = Ph; R¹ = pMeO-PhCH₂—; R³ = H; R² = —NHCONH₂; M = H; α¹ = L)

Prepared by method B from α Ureido-L-β-(p Methoxyphenyl) propionic acid.

Yield: 19%. νmax (KBr): 3300 (br.), 1775, 1640, 1515, 1250 and 700cm⁻¹. δ[(CD₃)₂SO]: 1.45 (3H.s. gem methyl), 1.58 (3H.s. gem methyl), 2.83 (2H.m. PhC$\underline{H}$₂), 3.72 (3H.s. C$\underline{H}$₃O), 4,28 (1H.s. C3 proton), 4.61 (1H.m. PhCH₂C$\underline{H}$), 5.35–5.93 (5H.m. β-lactams, PhC$\underline{H}$, —NHCON$\underline{H}_2$*), 6.27 (1H.d. —N$\underline{H}$CO—), 6.67–7.50 (9H.m. aromatic protons), 8.70 and 9.32 (2 × 1H.d. —N$\underline{H}$CO—*)

* Removed by $D_2O$

NH$_2$OH Assay: 81% Biochromatogram: Single zone $R_f$ 0.43.

EXAMPLE 43

D-α-[D-α-Guanidino-β-phenylpropionamido]-phenylacetamido penicillanic acid hydrochloride (R = Ph; R$^1$ = PhCH$_2$—, R$^3$ = H;

$R^2 = -NH-C{\displaystyle \diagup^{NH} \atop \diagdown_{NH_2}}$ .HCl ;

M = H α$^1$ = D)

Prepared by method E from D-α-Guanidino-β-phenyl propionic acid.

Yield: 21% νmax (KBr): 3330 (br.), 1768, 1663, 1602, 1525, 1458 1394, 1320, 703cm$^{-1}$. δ[(CD$_3$)$_2$SO]: 1.44 (3H.s. gem methyl), 1.57 (3H.s. gem methyl), 2.96–3.23 (2H.m. PhC$\underline{H}_2$—), 4.17 (1H.m. C3 proton), 4.61 (1H.m. PhCH$_2$C$\underline{H}$<), 5.30–5.94 (3H.m. β-lactams and PhC$\underline{H}$<), 7.11–7.71 (14H.m. aromatic protons and $-NH-C{\displaystyle \diagup^{NH} \atop \diagdown_{NH_2}}$ HCl* ), 8.14 –8.47 (1H.m.—N$\underline{H}$—$C{\displaystyle \diagup^{NH} \atop \diagdown_{NH_2}}$ HCl*), 8.82 and 9.12 (2 × 1H.m. —CON$\underline{H}$—*)

* removed by $D_2O$

NH$_2$OH Assay: 90%. Biochromatogram: Single zone $R_f$ 0.52.

EXAMPLE 44

D-α-[D,L-β-Methoxy-α-ureidopropionamido]-phenylacetamido penicillanic acid (R = Ph; R$^1$ = CH$_3$OCH$_2$; R$^3$ = H; R$^2$ = —NHCONH$_2$; M = H; α = D,L)

Prepared by method B from D-α-Ureido-β-methoxy propionic acid.

Yield: 23%. νmax (KBr): 3350 (br.), 1775, 1650, 1520, 1310, 1225, 1115 and 700cm$^{-1}$. δ[(CD$_3$)$_2$SO]: 1.45 (3H.s. gem methyl), 1.58 (3H.s. gem methyl), 3.27 (3H.d. C$\underline{H}_3$OCH$_2$—), 3.57 (2H.m. CH$_3$OC$\underline{H}_2$—), 4.18–4.75 (1H.m. —CH$_2$C$\underline{H}$<), 4.27 (1H.s. C3 proton), 5.23–5.98 (5H.m. β-lactams, —NHCON$\underline{H}_2$*, PhC$\underline{H}$<), 6.37 (1H.d. —N$\underline{H}$CO—*), 7.38 (5H.m. aromatic protons) 8.42 (1H.d. —CON$\underline{H}$—*), 9.14 (1H.m. —CON$\underline{H}$—*).

* Removed by $D_2O$

NH$_2$OH Assay: 98%. Biochromatogram: Single zone $R_f$ = 0.24.

EXAMPLE 45

Phthalid-3-yl D-α-[D-α-Guanidino-β-Phenylpropionamido] phenylacetamido penicillinate, hydrochloride (R = Ph ; R$^1$ = PhCH$_2$- ; R$^3$ = H ;

$R^2 = -NH-C{\displaystyle \diagup^{NH} \atop \diagdown_{NH_2}}$ .HCl ; M =

[phthalide structure] ; α$^1$ = D)

Prepared by method A from D-α-Guanidino-β-phenyl propionic acid.

Yield: 23% νmax (KBr): 3340 (br.), 1785, 1660, 1510, 1285, 980 755 and 705cm$^{-1}$. δ[(CD$_3$)$_2$SO]: 1.53 (6H.m. gemdimethyls), 3.03 (2.H.m. PhC$\underline{H}_2$CH), 4.56 (1H.s. C3 proton), 4.37–5.08 (1H.m. PhCH$_2$C$\underline{H}$C), 5.33–6.01 (3H.m. β-lactams and PhC$\underline{H}$), 7.52 (1H.s. Phthalide 3 proton), 6.95–8.05 (19H.m. aromatic protons and $NH-C{\displaystyle \diagup^{NH} \atop \diagdown_{NH_2}}$ .HCl), 8.05–9.49 (2 × 1H.m. —CON$\underline{H}$—*)

* Removed by $D_2O$

NH$_2$OH Assay: 91%. Biochromatogram: Single zone $R_f$ 0.87.

EXAMPLE 46

D-α-[L-β-Phenyl-α-ureidopropionamido]-phenylacetamido penicillanic acid (R = Ph; R$^1$ = PhCH$_2$; R$^3$ = H; R$^2$ = —NHCONH$_2$; M = H; α$^1$ = L)

Prepared by method Bi from D-α-Ureido-β-phenyl propionic acid.

Yield: 15% νmax (KBr): 3360 (Br.), 1775, 1650, 1525, 1315, 1230 and 705cm$^{-1}$. δ[(CD$_3$)$_2$SO]: 1.44 (3H.s. gem methyl), 1.59 (3H.s. gem methyl), 2.89 (2H.m. PhC$\underline{H}_2$—), 4.25 (1H.s. C3 proton), 4.68 (1H.m. PhC$\underline{H}_2$CH), 5.64 (5H.m. β-lactams NHCON$\underline{H}_2$*), PhC$\underline{H}$)), 6.27 (1H.d. —N$\underline{H}$CO—), 7.28 (10H.m. aromatic protons), 8.62 and 9.17 (2 × 1H.d. —CON$\underline{H}$—*)

* Removed by $D_2O$.

Biochromatogram: Single zone

EXAMPLE 47

D-α-[D,L-α-(3-ethylureido)-β-phenylpropionamido]-phenylacetamidopenicillanic acid (R = Ph- , R$^1$ = Ph-CH$_2$-,

R$^3$ = H, R$^2$ =NHCONHCH$_2$CH$_3$,

M = H, α$^1$ = D,L)

Prepared by method Bi from D,L-(3-ethylureido)-β-phenylpropionic acid.

Yield: 16% m.p. 174°–6°C (dec.) νmax(KBr): 3380 (broad), 1774, 1637, 1540, 1299, 1218 and 701cm$^{-1}$.

δ[(CD$_3$)$_2$SO]: 0.96 (3H.t. —NHCH$_2$C<u>H</u>$_2$), 1.44 (3H.s. gem methyl), 1.58 (3H.s. gem methyl), 2.96 (4H.m. PhC<u>H</u>$_2$CH<, —NHC<u>H</u>$_2$CH$_3$), 4.27 (1H.s. C3 proton), 4.59 (1H.m. PhCH$_2$C<u>H</u><), 5.38–6.17 (5H.m. β-lactams, PhC<u>H</u><, —NHCON<u>H</u>—*), 7.32 (10H.m. P<u>h</u>CH<, P<u>h</u>CH$_2$CH<), 8.58 (1H.m. —CON<u>H</u>—*), 9.12 (1H.m. —CON<u>H</u>—*).

* Removable with D$_2$O.

Hydroxylamine Assay: 92.9%. Biochromatography: R$_f$ = 0.71.

EXAMPLE 48

D-α-[D,L-β-(2-Thienyl)-α-ureidopropionamido]-phenylacetamidopenicillanic acid

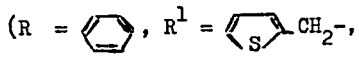

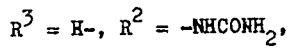

M = H, α$^1$ = D,L)

Prepared by method Bi from D,L-β-(2-thienyl)-α-ureidopropionic acid.

Yield: 25.9% νmax(KBr): 3355 (br.), 1773, 1648, 1537, 1307, 1226 and 701cm⁻¹. δ[(CD$_3$)$_2$SO]: 1.42 (3H.s. gem methyl), 1.56 (3H.s. gem methyl), 3.10 (2H.m. —C<u>H</u>$_2$CH<), 4.21 (1H.s. C3 proton), 4.50 (1H.m. —CH$_2$C<u>H</u><), 5.58 (5H.m. β-lactams, —NHCON<u>H</u>$_2$*, PhC<u>H</u>), 6.28 (1H.m. —N<u>H</u>CONH$_2$*), 6.89 (2H.m. thienyl 3- and 4-protons), 7.35 (6H.s. phenyl aromatics and thienyl 5-proton), 8.67 (1H.m. —CON<u>H</u>—*), 9.15 (1H.m. —CON<u>H</u>—*).

* Removable with D$_2$O.

Hydroxylamine Assay: 70.6%. Biochromatography: R$_f$ = 0.41.

EXAMPLE 49

Potassium D-α-[D-α-(3-ethylureido)-p-phenyl-propionamido]-phenylacetamidopenicilianate (R = Ph—, R$^1$ = PhCH$_2$—, R$^3$ = H—, R$^2$ = —NHCONHCH$_2$CH$_3$, N = K, α$^1$ = D)

Prepared by method Bi from D-α-(3-ethylureido)-β-phenylpropionic acid.

Yield: 65.3% νmax(KBr): 3350(br), 1774, 1630, 1540, 1225, 732 and 702cm⁻¹. δ[(CD$_3$)$_2$SO]: 0.95 (3H.t. J = 7Hz —NHCH$_2$C<u>H</u>$_3$), 1.45 (3H.s. gem-methyl), 1.58 (3H.s. gem-methyl), 2.75–3.35 (4H.m. PhC<u>H</u>$_2$CH, —NHC<u>H</u>$_2$CH$_3$ (J = 7Hz)), 4.28 (1H.s. C-3 proton), 4.61 (1H.m. PhCH$_2$C<u>H</u><), 5.4–6.3 (5H.m. β-lactams, PhC<u>H</u>, —NHCON<u>H</u>—*), 7.37 (10H.m. P<u>h</u>CH, P<u>h</u>CH$_2$CH<), 8.53 (1H.d. —CON<u>H</u>—*), 9.12 (1H.m. —CON<u>H</u>—*),

* removable in D$_2$O

Hydroxylamine Assay: 85.4%. Biochromatography: R$_f$ = 0.65.

EXAMPLE 50

D-α-[D-β-Phenyl-α-(3-n-propylureido)-propionamido]-phenylacetamidopenicillanic acid

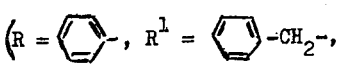

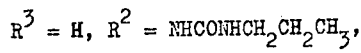

M = H, α$^1$ = D)

Prepared by method Bi from D-α-(3-n-propylureido)-propionic acid.

Yield: 70.3% νmax(KBr): 3320 (br.), 1772, 1633, 1540, 1222, 731 and 701cm⁻¹. δ[(CD$_3$)$_2$SO]: 0.81 (3H.t. —NHCH$_2$CH$_2$C<u>H</u>$_3$), 1.45 (3H.s gem methyl), 1.58 (3H.s. gem methyl), 2.7–3.3 (6H.m. PhC<u>H</u>$_2$CH<, —NHC<u>H</u>$_2$C<u>H</u>$_2$CH$_3$), 4.27 (1H.s. C-3 proton), 4.6 (1H.m. PhCH$_2$C<u>H</u><), 5.4–6.3 (5H.m. β-lactams, PhC<u>H</u><, —NHCON<u>H</u>—*), 7.31 (10H.m. P<u>h</u>CH<, P<u>h</u>CH$_2$CH<), 8.53 (1H.m. —CON<u>H</u>—*), 9.10 (1H.m. —CON<u>H</u>—*).

* Removable with D$_2$O

Hydroxylamine Assay: 94.7% Biochromatography: R$_f$ = 0.73

EXAMPLE 51

D-α-[D-β-Phenyl-α-(3-iso-propylureido)-propionamido]-phenylacetamidopenicillanic acid

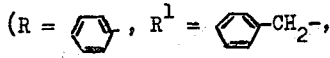

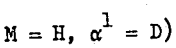

M = H, α$^1$ = D)

Prepared by method Bi from D-α-phenyl-α-(3-iso-propylureido-propionic acid.

Yield: 60% νmax (KBr): 3363 (br), 1772, 1626, 1533, 1230, 1128, 729 and 701 cm⁻¹. δ[(CD$_3$)$_2$SO]: 0.99 (6H.d. NHCH(C<u>H</u>$_3$)$_2$), 1.45 (3H.s. gem methyl), 1.58 (3H.s. gem methyl), 2.92 (2H.m. PhC<u>H</u>$_2$CH<), 3.3. (1H.m. —NHC<u>H</u>(CH$_3$)$_2$), 4.28 (1H.s. C-3 proton), 4.6 (1H.m. PhCH$_2$C<u>H</u><), 5.4–6.3 (5H.m. β-lactams, PhC<u>H</u><, —NHCON<u>H</u>—*), 7.23 (5H.s. P<u>h</u>CH$_2$CH<), 7.39 (5H.m. P<u>h</u>CH<), 8.4–9.5 (2H.m. 2 × —CON<u>H</u>—*).

*Removable with D$_2$O

Hydroxylamine Assay: 89.7%
Biochromatography: R$_f$ = 0.72

EXAMPLE 52

Potassium D-α-[D-α-(3-Cyclohexylureido)-β-phenylpropionamido]-phenylacetamidopenicillanate

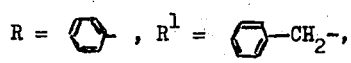

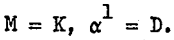

M = K, α$^1$ = D.

Prepared by method Bi from D-α-(3-cyclohexylureido)-β-phenylpropionic acid.

Yield: 57% νmax (KBr): 3330 (br.), 1762, 1628, 1546, 1392, 1320 and 701cm⁻¹. δ[(CD$_3$)$_2$SO]: 0.6–1.7

(10H.m cyclohexyl methylenes) 1.44 (3H.s. gem methyl), 1.54 (3H.s. gem methyl), 2.75–3.4 (3H.m. PhCH₂CH<,

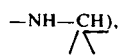

3.92 (1H.d. C-3 proton), 4.3–4.7 (1H.m. PhCH₂CH<), 5.2–5.6 (2H.m. β-lactams), 5.65–5.94 (1H.m. PhCH<), 6.1–6.5 (2H.m. —NHCONH—*), 7.23 (5H.s. PhCH₂CH<), 7.37 (5H.m. PhCH<), 8.4–9.0 (2H.m. 2 × —CONH—*)
* Removable with D₂O Hydroxylamine Assay: 85.9% Biochromatography: R_f = 0.73

EXAMPLE 53

Potassium D-α-[DL-α-(3-tert-butylureido)-β-phenylpropionamido] phenylacetamidopenicillanate.

(R = Ph; R¹ = PhCH₂—; R³ = H; R² = —NHCONHC(CH₃)₃; M = K; α¹ = D,L)

Prepared by method Bi from D,L-α-(3-tert-butylureido)-β-phenylpropionic acid.

Yield: 40.2%. νmax (KBr): 3360(br), 1774, 1645(br), 1540(br), 1456, 1214, 733 and 702 cm⁻¹ δ[(CD₃)₂SO]: 1.22 (9H.s. —NHC(CH₃)₃); 1.45(3H.s. gem dimethyl); 1.58(3H.s. gem dimethyl); 2.89(2H.m. PhCH₂CH<) 4.23(1H.s. C-3 proton); 4.53(1H.m. PhCH₂CH<) 5.35–6.15(5H.m. β-lactams, PhCH< and —NHCONH—*); 7.30 (10H.m. PhCH< and PhCH₂CH<); 8.51(1H.d. —CONH—*); 9.12(1H.d. —CONH—*).
* removable in D₂O.

Hydroxylamine Assay: 99.8%. Biochromatography: 1 zone at Rf 0.72.

EXAMPLE 54

D-β-[DL-β-(p-Hydroxyphenyl)-α-ureidopropionamido] phenylacetamidopenicillanic acid.

R = Ph; R¹ = p—HO—PhCH₂; R³ = H; R² = —NHCONH₂; M = h; α¹ = D,L

Prepared by method B from D,L-β-(p-hydroxyphenyl)-α-ureidopropionic acid.

Yield: 80%. νmax (KBr): 3350(br), 1772, 1650, 1517, 1230, and 703 cm⁻¹. δ[(CD₃)₂SO]: 1.44(3H.s. gem methyl); 1.57 (3H.s. gem methyl) ~2.8 (2H.m. —CH₂CH<); 4.29 (1H.s. C-3 proton) ~4.5 (1H.m —CH₂CH<); 5.35–5.87 (5H.m. β-lactams, PhCH< and —NHCONH₂*); 6.27 (1H.d. —NHCONH₂*); 6.67 (2H.d. o-protons in p—HO—Ph ring); 6.99 (2H.d. m-protons in p—HO—Ph ring); 7.30(5H. broad s. PhCH); 8.47 (1H.m. —CONH—*) 9.12 (1H.m. —CONH—*)
* removable with D₂O.

Hydroxylamine Assay: 79.4%. Biochromatography: 1 Zone at Rf 0.27.

EXAMPLE 55

D-α-[D,L-β-(m-Hydroxyphenyl)-α-ureidopropionamido]-phenylacetamido penicillanic acid.

(R = Ph, R¹ = m—HO—PhCH₂—, R³ = H, R² = —NHCONH₂, M = H, α¹ = D,L)

Prepared by method B from D,L-β-(m-hydroxyphenyl)-α-ureidopropionic acid.

Yield: 46%. νmax (KBr): 3360(br), 1775, 1625, 1531, 1236, 1164, and 703 cm⁻¹. δ[(CD₃)₂SO]: 1.45 (3H.s. gem methyl); 1.58 (3H.s. gem methyl); ~2.8 (2H.m. —CH₂CH<); 4.32 (1H.s. C-3 proton) 4.55 (1H.m. —CH₂CH<); 5.40–5.90 (5H.m. β-lactams, PhCH< and —NHCONH₂*); 6.35 (1H.d. —NHCONH₂*) 6.55–7.15 (4H.m. m—HO—Ph—aromatics); 7.32 (5H. broad s. PhCH<); 8.52 (1H.d. —CONH—*); 9.16 (1H.m. —CONH—*)
* removable with D₂O.

Hydroxylamine Assay: 93.7%. Biochromatography: 1Zone at Rf 0.39.

EXAMPLE 56

D-α-[D-β-Phenyl-α-ureidopropionamido]-(2-thienyl)-acetamidopenicillanic acid.

Prepared by method Bviii with D-β-phenyl-α-ureidopropionic acid.

Yield: 44.8%. νmax (Nujol): 3310(br), 1785, 1668, 1539, 1233 and 701 cm⁻¹. δ[(CD₃)₂SO]: 1.47(3H.s. gem methyl); 1.60(3H.s. gem methyl; ~3(2H.m. PhCH₂CH<); 3.9–4.4(1H.s. PhCH₂CH<) 4.26(1H.s. C-3 proton); 5.3–6.6 (6H.m. β-lactams, ThCH<, and —NHCONH₂*); 7.28(8H.m. PhCH₂CH< and ThCH<); 7.7–9.5 (2H.m. 2 × —CONH—*)
* removable with D₂O.

Hydroxylamine Assay: 78.2%. Biochromatography: One zone at Rf 0.62 (plus faint zone at Rf 0.27 due to starting amino penicillin.)

EXAMPLE 57

D-α-[D-β-Phenyl-α-ureidopropionamido]-valeramidopenicillanic acid.

(R = CH₃(CH₂)₂—, R¹ = PhCH₂—, R³ = H, R² = )NHCONH₂, M = H, α¹ = D)

Prepared by method Bvii from D-β-phenyl-α-ureidopropionic acid.

Yield: 30%. νmax (KBr): 3340(br), 1774, 1650, 1530, 1231, and 703cm⁻¹ δ[(CD₃)₂SO]: 0.92 (3H.m. CH₃(CH₂)₂—); 1.1–1.7 (10H.m. gemdimethyls, CH₃(CH₂)₂—); 2.85–3.0 (2H.m. PhCH₂CH<); 4.3–4.7 (2H.m. CH₃(CH₂)₂CH<, PhCH₂CH<); 4.34 (1H.s. C-3 proton); 5.47–5.8 (4H.m. β-lactams, —NHCONH₂*); 6.30 (1H.d. —NHCONH₂*); 7.27 (5H.s. aromatics); 8.12 (1H.d. —CONH—*); 8.81 (1H.m. —CONH—*)
* removable with D₂O.

Hydroxylamine Assay: 78%. Biochromatography: 1 zone at Rf 0.59.

EXAMPLE 58

D-α-[D-β)Phenyl-α-ureidopropionamido]-cyclopropylacetamidopenicillanic acid.

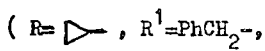

Prepared by method Bvi from D-β-phenyl-α-ureidopropionic acid.

Yield: 50%. νmax (KBr): 3345(br), 1772, 1645,(br), 1527, 1230 and 703 cm$^{-1}$ δ [(CD$_3$)$_2$SO]: 0.25–1.25H.m. cyclopropyl ring protons) 1.51 (3H.s. gem methyl); 1.63 (3H.s. gem methyl); 2.92 (2H.m. PhC$\underline{H}_2$—);

4.05 (1H.m. ▷—C$\underline{H}$⋦);

4.3 (1H.s. PhCH$_2$C$\underline{H}$<) 5.5–5.8 (4H.m. β-lactams and —CONH$_2$*); 6.18 (1H.d. —CON$\underline{H}$—*) 7.2–7.4 (5H.m. aromatic protons); 8.18 and 8.93 (2 × 1H.d. —CON$\underline{H}$—*)

* removed by D$_2$O.

Hydroxylamine Assay: 95.6%. Biochromatography: 1 zone at Rf 0.37

EXAMPLE 59

D-α-[D-β-Phenyl-α-ureidopropionamido]-β-phenyl-propionamidopenicillanic acid (R = R$^1$ = PhCH$_2$—, R$^3$ = H, R$^2$ — —NHCONH$_2$, M = H, α$^1$ = D)

Prepared by method Bix from D-p-phenyl-α-ureidopropionic acid.

Yield: 40% νmax (KBr): 3322(br), 1725, 1638, 1534, 1302, 1231, 702cm$^{-1}$ δ[(CD)$_3$SO]: 1.51 (3H.s. gem-methyl), 1.65 (3H.s. gem-methyl), 3.0 (4H.m. PhC$\underline{H}_2$, PhC$\underline{H}_2$), 4.32 (1H.s. C-3 proton), 4.4 and 4.8 (2 × 1H.m. PhCH$_2$C$\underline{H}$<), 5.52 (2H.m. β-lactams), 6.1 (1H.m. — CON$\underline{H}$—), 7.1–7.4 (10H.m. aromatic protons), 8.20 and 8.78 (2 × 1H.m. —CON$\underline{H}$*—)

* removed by D$_2$O.

NH$_2$OH Assay: 87% Biochromatography: Single zone R$_f$ 0.40

EXAMPLE 60

D-α-[D-α-Ureido-n-heptanamido]-phenylacetamido penicillanic acid (R = Ph; R$^1$ = CH$_3$(CH$_2$)$_5$; R$^3$ = H; R$^2$ = —NHCONH$_2$; M = H; α$^1$ = D)

Prepared by method Bi, from D-Ureidoheptanoic acid. Yield: 45% νmax (KBr): 3380(br), 1763, 1650, 1600, 1538, 1401, 1323, 1234, 699cm$^{-1}$. δ[(CD$_3$)$_2$SO]: 0.87 (3H.m. C$\underline{H}_3$(CH$_2$)$_5$), 1.0–2.0 (10H.m. CH$_3$(C$\underline{H}_2$)$_5$), 1.47 (3H.s. gem-methyl), 1.56 (3H.s. gem-methyl), 3.97 (1.H.s. C-3 proton), 3.4–3.8 (1H.m (CH$_2$)$_5$C$\underline{H}$<), 5.3–5.9 (5H.m β-lactams, PhC$\underline{H}$<,—CONH$_2$ *), 7.2–7.6 (5H.m. aromaticprotons), 6.6, 8.7 and 8.9 (3 × 1H.m. —CON$\underline{H}$* —)

* removed by D$_2$O

NH$_2$OH Assay : 37%. Biochromatography: Single zone R$_f$ 0.67

EXAMPLE 61

D-α-[D-α-Ureido-n-hexanamido]-phenylacetamido penicillanic acid (R = Ph, R$^1$= CH$_3$(CH$_2$)$_3$, R$^3$ = H, R$^2$ = —NHCONH$_2$, M = H, α$^1$= D)

Prepared by method Bi using D-α-ureidohexanoic acid.

Yield: 60% νmax (KBr) : 3340, 1772, 1640, 1312, 1234, 700cm$^{-1}$. δ[(CD$_3$)$_2$SO]: 0.84 (3H.m C$\underline{H}_3$(CH$_2$)$_3$, 1.0–1.8 (6H.m. CH$_3$(C$\underline{H}_2$)$_3$, 1.42 (3H.s. gem-methyl), 1.54 (3H.s. gem-methyl), 4.23 (1H.s. C-3 proton), 4.23 (1H.m. CH$_3$(CH$_2$)$_3$C$\underline{H}$<), 5.4–5.9 (5H.m. β-lactams, PhC$\underline{H}$< and CONH$_2$*), 6.25 (1H.m. —CON$\underline{H}$—), 7.40 (5H.m. aromatic protons), 8.49 and 9.08 (2 × 1H.d. —CON$\underline{H}$* —)

*removed by D$_2$O.

Hydroxylamine Assay: 73%
Biochromatography: R$_f$= 0.59

EXAMPLE 62

D-α-[D-β-(1,4-Cyclohexadienyl-α-ureidopropionamido]-(p-hydroxyphenyl)acetamidopenicillanic acid (R =$_p$ -HO-Ph), R$^1$ = ⟨⟩—CH$_2$-

R$^3$ = H, R$^2$ = -NHCONH$_2$, M = H,

α$^1$ = D)

Prepared by method Bii using D-β-(1,4-cyclohexadienyl)-α-ureidopropionic acid

Yield: 50% νmax (KBr): 3330(br), 1770, 1640, 1510, 1223, 961, and 840cm$^{-1}$. δ[(CD$_3$)$_2$SO] : 1.45 (3H.s. gem-methyl); 1.58 (3H.s. gem-methyl); 2.1–2.4

(2H.m. ⟨⟩—C$\underline{H}_2$CH<);

2.61 (4H. broad s. cyclohexadiene methylenes); 4.24

(1H.s. C-3 proton); 4.2–4.5 (1H.m. ⟨⟩CH$_2$C$\underline{H}$ <)

5.35–5.8 (8H.m. β-lactams,

HO—⟨⟩—CH< cyclohexadiene methines,

-NHCON$\underline{H}_2^*$ );

5.9–6.2 (1H.m. —N$\underline{H}$CONH$_2$*); 6.72

(2H.d. HO—⟨$\underline{H}$⟩—CH
            $\underline{H}$ 7.23 (2H.d. HO—⟨$\underline{H}$⟩—CH<),
             $\underline{H}$ 8.3 (1H.m. —CON$\underline{H}$—*); 8.9 (1H.m. —CONH*).

* removable with D$_2$O

Hydroxylamine Assay: 98.2% Biochromatography: R$_f$ = 0.41

EXAMPLE 63

D-α-[D-β-(1,4-Cyclohexadienyl)-α-(3-ethylureido)-propionamido]-(p-hydroxyphenyl)-acetamido-penicillanic acid (R = HO—⟨⟩— , R$^1$ = ⟨⟩—CH$_2$-,

R$^3$ = H-, R$^2$= -NHCONHCH$_2$CH$_3$,

M = H, α$^1$ = D)

Prepared by method Bii from D-β-(1,4-cyclohexadienyl)-α-(3-ethylureido)-propionic acid.

Yield: 20%

νmax (KBr): 3350 (br), 1760, 1510, 1371, 1258, 1220 and 781cm⁻¹. δ[(CD₃)₂SO]: 1.1–1.7 (9H.m. gem dimethyls, —NHCH₂CH₃) 1.9–2.2

(2H.m. 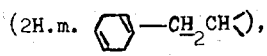, 2.45–2.75 (4H.m. cyclohexadiene methylenes), 3.9–4.5

(4H.m. NHCH₂CH₃, C-3 proton and

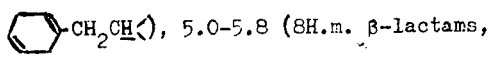, 5.0–5.8 (8H.m. β-lactams,

, cyclohexadiene methines, —NHCONH*—), 6.6–7.6 (4H.m aromatics), 8.3–9.2 (2H.m 2 × —CONH*—).

* Removable in D₂O

Hydroxylamine Assay: 88% Biochromatography: R_f = 0.44 (plus 2 minor zones)

EXAMPLE 64

D-α-[D-α-Acetamido-n-hexanamido]-(p-hydroxyphenyl)-acetamidopenicillanic acid

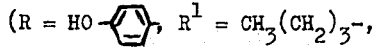

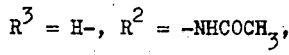

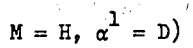

Prepared by method Bii from D-α-acetamido-n-hexanoic acid.

Yield: 30% νmax (KBr): 3310(br.), 1770, 1645, 1510, 1374, 1210, 1173cm⁻¹. δ[(CD₃)₂SO]: 0.8–1.8 (9H.m. CH₃(CH₂)₃—), 1.43 (3H.s. gem methyl), 1.54 (3H.s. gem methyl), 1.92 (3H.d. COCH₃) 4.28 (1H.s. C3 proton), 4.38 (1H.m CH₂CH<), 5.4–5.8 (3H.m. β-lactams and PhCH<), 6.22 (1H.d. —CONH*—), 7.0–7.6 (4H.m. aromatic protons), 8.25 and 9.3 (2 × 1H.m. —CONH—*)

* Removed by D₂O

Hydroxylamine Assay: 124.6% Biochromatography: R_f = 0.35 (plus small zone due to amino-penicillin).

We claim:
1. A penicillin of formula (I):

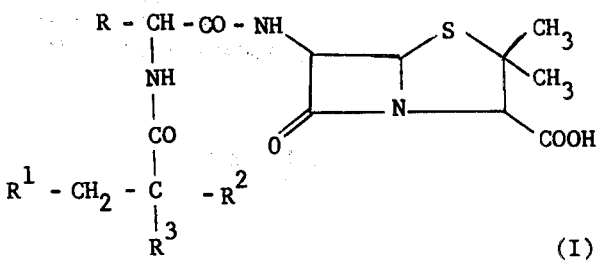

wherein

R is phenyl, hydroxyphenyl, halophenyl, nitrophenyl, alkoxyphenyl having 1–3 carbon atoms in the alkoxy part, aminophenyl, 2- or 3-thienyl, cycloalkyl having 3–7 carbon atoms in the cyclo part, cycloalkenyl having 5–7 carbon atoms in the cyclo part, or alkyl having 1–4 carbon atoms;

$R^1$ is cyclohexa-1,4-dienyl, cyclopropyl or cyclohexyl;

$R^2$ is

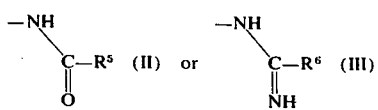

in which $R^5$ is amino, mono- or di-alkylamino having 1–4 carbon atoms in the alkyl part, cyclohexylamino, hydrogen, alkyl of 1–4 carbon atoms or phenyl, and $R^6$ is amino, mono- or di-alkylamino having 1–4 carbon atoms in the alkyl part or cyclohexylamino;

$R^3$ is hydrogen or alkyl of 1–3 carbon atoms; or a pharmaceutically acceptable salt or a pharmaceutically acceptable hydrolyzable ester which converts to the free acid from in vivo.

2. A penicillin of claim 1 wherein the carbon atom attached to R is in the D-configuration.

3. A penicillin of claim 1 wherein the carbon atom attached to $R^2$ is in the D-configuration.

4. A penicillin of claim 1 wherein R is phenyl, 4-hydroxyphenyl or 3-thienyl.

5. A penicillin of claim 1 wherein $R^3$ is hydrogen.

6. A penicillin of claim 1 wherein, when $R^2$ is (II), $R^5$ is amino or hydrogen or, when $R^2$ is (III), $R^6$ is amino.

7. A penicillin of claim 1 wherein the ester is phthalidyl, 5,6-dimethoxyphthalidyl, pivaloyloxymethyl or acetoxymethyl.

8. A penicillin of claim 1 wherein the salt is a base addition or acid addition salt.

* * * * *